US011981961B2

(12) United States Patent
Tsavachidou

(10) Patent No.: US 11,981,961 B2
(45) Date of Patent: May 14, 2024

(54) METHODS FOR CONSTRUCTING COPIES OF NUCLEIC ACID MOLECULES

(71) Applicant: Vastogen, Inc., Houston, TX (US)

(72) Inventor: Dimitra Tsavachidou, Houston, TX (US)

(73) Assignee: Vastogen, Inc., Houston, TX (US)

( * ) Notice: Subject to any disclaimer, the term of this patent is extended or adjusted under 35 U.S.C. 154(b) by 413 days.

(21) Appl. No.: 16/480,655

(22) PCT Filed: Jan. 21, 2018

(86) PCT No.: PCT/US2018/014598
§ 371 (c)(1),
(2) Date: Jul. 24, 2019

(87) PCT Pub. No.: WO2018/140329
PCT Pub. Date: Aug. 2, 2018

(65) Prior Publication Data
US 2019/0352706 A1 Nov. 21, 2019

Related U.S. Application Data

(60) Provisional application No. 62/450,070, filed on Jan. 24, 2017, provisional application No. 62/451,734, (Continued)

(51) Int. Cl.
*C12P 19/34* (2006.01)
*C12Q 1/6855* (2018.01)

(52) U.S. Cl.
CPC ..... *C12Q 1/6855* (2013.01); *C12Q 2521/307* (2013.01); *C12Q 2525/301* (2013.01); *C12Q 2525/307* (2013.01); *C12Q 2531/125* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS 6,329,178 B1   12/2001   Patel et al.
6,395,524 B2   5/2002    Loeb et al.
(Continued)

FOREIGN PATENT DOCUMENTS

EP    2620510 B1       10/2016
WO    WO 2007/010251 A2   1/2007
(Continued)

OTHER PUBLICATIONS

"Rolling circle replication" from Wikipedia. Printed on Dec. 16, 2021.*
(Continued)

*Primary Examiner* — Frank W Lu
(74) *Attorney, Agent, or Firm* — Wolf, Greenfield & Sacks, P.C.

(57) ABSTRACT

Methods for constructing consecutively connected copies of nucleic acid molecules are disclosed. Consecutively connected copies of nucleic acid molecules can be used to perform sequencing of the same nucleic acid molecules several times, improving overall accuracy of sequencing. Connected copies of nucleic acid molecules can be constructed by circularizing nucleic acid molecules, performing rolling circle amplification and debranching with nicking and polymerases comprising 5'-3' exonuclease and/or flap endonuclease activity.

4 Claims, 27 Drawing Sheets

Specification includes a Sequence Listing.

Related U.S. Application Data filed on Jan. 29, 2017, provisional application No. 62/473,700, filed on Mar. 20, 2017, provisional application No. 62/506,706, filed on May 16, 2017, provisional application No. 62/516,263, filed on Jun. 7, 2017, provisional application No. 62/576,974, filed on Oct. 25, 2017, provisional application No. 62/576,992, filed on Oct. 25, 2017.

(56) References Cited

U.S. PATENT DOCUMENTS

| | | | |
|---|---|---|---|
| 6,602,695 | B2 | 8/2003 | Patel et al. |
| 7,037,687 | B2 | 5/2006 | Williams et al. |
| 7,754,429 | B2 | 7/2010 | Rigatti et al. |
| 7,767,400 | B2 | 8/2010 | Harris |
| 7,981,604 | B2 | 7/2011 | Quake |
| 8,486,627 | B2 | 7/2013 | Ma |
| 8,518,640 | B2 | 8/2013 | Drmanac et al. |
| 2007/0048748 | A1 | 3/2007 | Williams et al. |
| 2008/0242560 | A1 | 10/2008 | Gunderson et al. |
| 2016/0230222 | A1 | 8/2016 | Liu |

FOREIGN PATENT DOCUMENTS

| | | |
|---|---|---|
| WO | WO 2014/140309 A1 | 9/2014 |
| WO | WO 2015/167972 A1 | 11/2015 |
| WO | WO 2016/195963 A1 | 12/2016 |
| WO | WO 2019/086531 A1 | 5/2019 |

OTHER PUBLICATIONS

Zhao et al., Rolling circle amplification: applications in nanotechnology and biodetection with functional nucleic acids. Angew. Chem. Int. Ed., 47(34), 6330-6337, 2008.*
Ali et al., Rolling circle amplification: a versatile tool for chemical biology, materials science and medicine. Chem. Soc. Rev., 43(10), 3324-3341, 2014.*
Extended European Search Report for Application No. EP 18744669.5, dated Sep. 10, 2020.
Mehta et al., A new full-length virus genome sequencing method reveals that antiviral RNAi changes geminivirus populations in field-grown cassava. bioRxiv. May 7, 2018. doi: 10.1101/168724. 24 pages.
Mehta et al., Full-length sequencing of circular DNA viruses and extrachromosomal circular DNA using CIDER-Seq. Nat Protoc. 2020; 15: 1673-1689. doi: 10.1038/s41596-020-0301-0.
Wang et al., Genome sequencing accuracy by RCA-seq versus long PCR template cloning and sequencing in identification of human papillomavirus type 58. Cell Biosci. 2014; 4: 5. EPub Jan. 13, 2014. doi: 10.1186/2045-3701-4-5.
EP 18744669.5, dated Sep. 10, 2020, Extended European Search Report.
International Search Report and Written Opinion for Application No. PCT/US2018/014598, dated Apr. 24, 2018.
International Preliminary Report on Patentability for Application No. PCT/US2018/014598, dated Aug. 8, 2019.
[No Author Listed] Lucigen MA126E-EZ-Tn5-Transposase manual. Retrieved from http://www.lucigen.com/docs/manuals/MA126E-EZ-Tn5-Transposase.pdf. Mar. 10, 2017. 6 pages.
Bellendir et al., Substrate preference of Gen endonucleases highlights the importance of branched structures as DNA damage repair intermediates. Nucleic Acids Res. May 19, 2017;45(9):5333-5348. doi: 10.1093/nar/gkx214.
Bermejo et al., Preventing replication stress to maintain genome stability: resolving conflicts between replication and transcription. Mol Cell. Mar. 30, 2012;45(6):710-8. doi: 10.1016/j.molcel.2012. 03.001.
Caruccio, Preparation of next-generation sequencing libraries using Nextera™ technology: simultaneous DNA fragmentation and adaptor tagging by in vitro transposition. Methods Mol Biol. 2011;733:241-55. doi: 10.1007/978-1-61779-089-8_17.
Chan et al., GEN1 promotes Holliday junction resolution by a coordinated nick and counter-nick mechanism. Nucleic Acids Res. Dec. 15, 2015;43(22):10882-92. doi: 10.1093/nar/gkv1207. Epub Nov. 17, 2015.
Ciccia et al., Identification and characterization of the human mus81-eme1 endonuclease. J Biol Chem. Jul. 4, 2003;278(27):25172-8. Epub Apr. 29, 2003.
Dickie et al., The site-specific cleavage of synthetic Holliday junction analogs and related branched DNA structures by bacteriophage T7 endonuclease I. J Biol Chem. Oct. 25, 1987;262(30):14826-36.
Goodwin et al., Oxford Nanopore Sequencing and de novo Assembly of a Eukaryotic Genome. bioRxiv 013490 preprint. Epub Jan. 6, 2015. doi: http://dx.doi.org/10.1101/013490. 15 pages.
Heiter et al., Site-specific DNA-nicking mutants of the heterodimeric restriction endonuclease R.BbvCI. J Mol Biol. May 6, 2005;348(3):631-40.
Higgins et al., The nicking endonuclease N.BstNBI is closely related to Type IIs restriction endonucleases MlyI and PleI. Nucleic Acids Res. Jun. 15, 2001;29(12):2492-2501. doi: 10.1093/nar/29. 12.2492.
Ishino et al., Mechanisms of maintaining genetic stability by homologous recombination. Chem Rev. Feb. 2006;106(2):324-39.
Landthaler et al., I-BasI and I-Hmul: two phage intron-encoded endonucleases with homologous DNA recognition sequences but distinct DNA specificities. J. Mol. Biol. Mar. 9, 2006;358(4):1137-1151. DOI: 10.1016/j.jmb.2006.02.054.
Li et al., INC-Seq: accurate single molecule reads using nanopore sequencing. bioRxiv preprint. Epub Jan. 27, 2016. doi: http://dx.doi.org/10.1101/038042. 22 pages.
Li et al., INC-Seq: accurate single molecule reads using nanopore sequencing. Gigascience. Aug. 2, 2016;5(1):34. doi: 10.1186/s13742-016-0140-7.
Morgan et al., Characterization of the specific DNA nicking activity of restriction endonuclease N.BstNBI. Biol Chem. Nov. 2000;381(11):1123-5.
Mullenix et al., Rolling Circle Amplification Improves Sensitivity in Multiplex Immunoassays on Microspheres. Clin Chem. Oct. 2002;48(10):1855-1858.
Myllykangas et al., Targeted sequencing library preparation by genomic DNA circularization. BMC Biotechnol. Dec. 14, 2011;11:122. doi: 10.1186/1472-6750-11-122. 12 pages.
Natsoulis et al., A flexible approach for highly multiplexed candidate gene targeted resequencing. PLoS One. 2011;6(6):e21088. doi: 10.1371/journal.pone.0021088. Epub Jun. 30, 2011.
Peters et al., Accurate whole genome sequencing and haplotyping from 10-20 human cells. Nature. Jul. 12, 2012;487(7406): 190-195. Epub Jul. 11, 2012. doi: 10.1038/nature11236. Author Manuscript.
Postow et al., Positive torsional strain causes the formation of a four-way junction at replication forks. J Biol Chem. Jan. 26, 2001;276(4):2790-6. Epub Oct. 30, 2000.
Postow et al., Topological challenges to DNA replication: conformations at the fork. Proc Natl Acad Sci U S A. Jul. 17, 2001;98(15):8219-26.
Rass et al., Mechanism of Holliday junction resolution by the human GEN1 protein. Genes Dev. Jul. 15, 2010;24(14):1559-69. doi: 10.1101/gad.585310.
Rass, Resolving branched DNA intermediates with structure-specific nucleases during replication in eukaryotes. Chromosoma. Dec. 2013;122(6):499-515. doi: 10.1007/s00412-013-0431-z. Epub Sep. 6, 2013.
Samuelson et al., The isolation of strand-specific nicking endonucleases from a randomized SapI expression library. Nucleic Acids Res. 2004; 32(12): 3661-3671. EPub Jul. 9, 2004. doi: 10.1093/nar/gkh674.
Schmidt et al., Intramolecular and intermolecular DNA ligation mediated by topoisomerase II. J Mol Biol. Aug. 5, 1994;241(1):18-25.
Subramanian et al., p53 Monitors replication fork regression by binding to "chickenfoot" intermediates. J Biol Chem. Dec. 30, 2005;280(52):42568-72. Epub Oct. 4, 2005.

(56) References Cited

OTHER PUBLICATIONS

Travers et al., A flexible and efficient template format for circular consensus sequencing and SNP detection. Nucleic Acids Res. Aug. 2010;38(15):e159. doi: 10.1093/nar/gkq543. Epub Jun. 22, 2010.
Walker et al., Isothermal in vitro amplification of DNA by a restriction enzyme/DNA polymerase system. Proc Natl Acad Sci U S A. Jan. 1, 1992; 89(1): 392-396. doi: 10.1073/pnas.89.1.392.
Wang et al., Preparation of DNA substrates for in vitro mismatch repair. Mol Biotechnol. Jun. 2000;15(2):97-104.
Wyatt et al., Holliday Junction Resolvases. Cold Spring Harb Perspect Biol. Sep. 2014; 6(9): a023192. doi: 10.1101/cshperspect. a023192. 31 pages.
Xu et al., Engineering a nicking endonuclease N.AlwI by domain swapping. PNAS Nov. 6, 2001:98(23);12990-12995. doi: https://doi.org/10.1073/pnas.241215698.
Zhang et al., Sequencing genomes from single cells by polymerase cloning. Nat Biotechnol. Jun. 2006;24(6):680-6. Epub May 28, 2006.
Zhu et al., Engineering strand-specific DNA nicking enzymes from the type IIS restriction endonucleases BsaI, BsmBI, and BsmAI. J Mol Biol. Mar. 26, 2004;337(3):573-83.
PCT/US2018/014598, dated Apr. 24, 2018, International Search Report and Written Opinion.
PCT/US2018/014598, dated Aug. 8, 2019, International Preliminary Report on Patentabiltiy.

* cited by examiner

METHODS FOR CONSTRUCTING COPIES OF NUCLEIC ACID MOLECULES

RELATED APPLICATIONS

This Application is a national stage filing under 35 U.S.C. 371 of International application number PCT/US2018/014598, filed Jan. 21, 2018, and claims priority under 35 U.S.C. § 119(e) to U.S. Provisional application No. 62/576,974, filed Oct. 25, 2017, U.S. Provisional application No. 62/576,992, filed Oct. 25, 2017, U.S. Provisional application No. 62/516,263, filed Jun. 7, 2017, U.S. Provisional application No. 62/506,706, filed May 16, 2017, U.S. Provisional application No. 62/473,700, filed Mar. 20, 2017, U.S. Provisional application No. 62/451,734, filed Jan. 29, 2017 and U.S. Provisional application No. 62/450,070, filed Jan. 24, 2017, each of which is herein incorporated by reference in its entirety.

SEQUENCE LISTING

The sequence listing, which comprises the DNA sequence described herein is hereby incorporated by reference in its entirety.

FIELD

The methods provided herein relate to the field of nucleic acid sequencing.

BACKGROUND

Nucleic acid sequence information is important for scientific research and medical purposes. The sequence information enables medical studies of genetic predisposition to diseases, studies that focus on altered genomes such as the genomes of cancerous tissues, and the rational design of drugs that target diseases. Sequence information is also important for genomic, evolutionary and population studies, genetic engineering applications, and microbial studies of epidemiologic importance. Reliable sequence information is also critical for paternity tests and forensics.

There is a constant need for new technologies that will lower the cost and increase the quality and amount of sequenced output. A promising technology that has the potential to revolutionize sequencing by simplifying the process and lowering the cost is nanopore-based detection. Nanopores are tiny holes that allow DNA translocation through them, which causes detectable disruptions in ionic current according to the sequence of the traversing DNA Sequencing at single-nucleotide resolution using nanopore devices is performed with high reported error rates (Goodwin et al., 2015). Since these errors occur randomly during sequencing, repeating the sequencing procedure for the same DNA strands several times will generate sequencing results based on consensus derived from replicate readings, thus increasing overall accuracy and reducing overall error rates.

SUMMARY

The methods disclosed herein relate to nucleic acid sequencing. Methods for constructing consecutively connected copies of nucleic acid molecules are disclosed.

Certain embodiments disclosed herein pertain to a method of constructing debranched constructs comprising copies of a nucleic acid molecule, said method applied to one or more nucleic acid molecules, and said method comprising the steps of (i) Circularizing a nucleic acid molecule by attaching it to at least one adaptor comprising at least part of at least one nicking endonuclease recognition site, (ii) Performing rolling-circle amplification; (iii) Exposing to nicking endonucleases recognizing said recognition site, so that nicks are produced only to one side of double-stranded regions of constructs produced in (ii); and (iv) Exposing to polymerases comprising 5'-3' exonuclease and/or flap endonuclease activity. In related embodiments, ligation of constructs produced in step (iv) can be performed to adaptors suitable for sequencing.

Other embodiments disclosed herein are related to a method of constructing copies of a nucleic acid molecule, said method applied to one or more nucleic acid molecules, and said method comprising the steps of: (i) Performing rolling circle amplification; (ii) Debranching with resolvases, thereby resolving three-way junctions and other branched products; and (iii) treating with polymerases comprising 5'-3' exonuclease activity and/or ligases, thereby rescuing nicked, gapped or flap-comprising products from further degradation.

Other embodiments disclosed herein are related to a method of producing debranched constructs comprising copies of a circular nucleic acid molecule, said circular nucleic acid molecule comprising a strand comprising at least one segment with a sequence that can be recognized by a sequence-specific nicking endonuclease in the event that said segment of said strand is annealed to another segment with a sequence complementary to said sequence of said segment, said sequence not having its complementary sequence being present in said strand, said method applied to one or more circular nucleic acid molecules, and said method comprising the steps of: (i) exposing said circular nucleic acid molecule to a reaction solution comprising nucleotides and strand-displacing polymerases to produce branched constructs comprising multiple copies of said circular nucleic acid molecule; and (ii) debranching said branched constructs, by comprising the steps of: (a) exposing to nicking endonucleases recognizing said sequence, thereby producing nicks on said branched constructs; and (b) exposing to polymerases comprising 5'-3' exonuclease and/or flap nuclease activity to extend 3' ends at the nicks produced in (a), thereby producing debranched double-stranded constructs.

BRIEF DESCRIPTION OF THE DRAWINGS

In the detailed description of various embodiments usable within the scope of the present disclosure, presented below, reference is made to the accompanying drawings, in which.

DETAILED DESCRIPTION

Figure 1A:
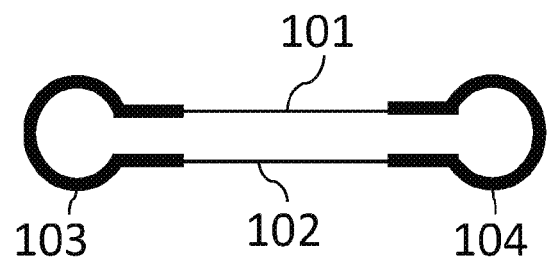
FIG. 1A is a schematic diagram of a circular nucleic acid molecule.

Methods described herein construct copies of a nucleic acid molecule that are consecutively connected to the nucleic acid molecule. Such copies are useful because they can be sequenced consecutively by a sequencer such as a nanopore device, enabling replicate readings, thus improving overall sequencing accuracy.

We show the particulars herein by way of example and for purposes of illustrative discussion of the embodiments. We present these particulars to provide what we believe to be the most useful and readily understood description of the principles and conceptual aspects of various embodiments of the disclosure. In this regard, we make no attempt to show structural details in more detail than is necessary for the fundamental understanding of the disclosed methods. We intend that the description should be taken with the drawings. This should make apparent to those skilled in the art how the several forms of the disclosed methods are embodied in practice.

Terms and Definitions

We mean and intend that the following definitions and explanations are controlling in any future construction unless clearly and unambiguously modified in the following examples or when application of the meaning renders any construction meaningless or essentially meaningless. In cases where the construction of the term would render it meaningless or essentially meaningless, we intend that the definition should be taken from Webster's Dictionary 3rd Edition.

"Nucleotide" as used herein refers to a phosphate ester of a nucleoside, e.g., a mono-, or a triphosphate ester. A nucleoside is a compound consisting of a purine, deazapurine, or pyrimidine nucleoside base, e.g., adenine, guanine, cytosine, uracil, thymine, 7-deazaadenine, that can be linked to the anomeric carbon of a pentose sugar, such a ribose, 2'-deoxyribose, or 2', 3'-di-deoxyribose. The most common site of esterification is the hydroxyl group connected to the C-5 position of the pentose (also referred to herein as 5' position or 5' end). The C-3 position of the pentose is also referred to herein as 3' position or 3' end. The term "deoxyribonucleotide" refers to nucleotides with the pentose sugar 2'-deoxyribose. The term "ribonucleotide" refers to nucleotides with the pentose sugar ribose. The term "dideoxyribonucleotide" refers to nucleotides with the pentose sugar 2', 3'-di-deoxyribose.

A nucleotide may be incorporated and/or modified, in the event that it is stated as such, or implied or allowed by context.

"Complementary" generally refers to specific nucleotide duplexing to form canonical Watson-Crick base pairs, as is understood by those skilled in the art. For example, two nucleic acid strands or parts of two nucleic acid strands are said to be complementary or to have complementary sequences in the event that they can form a perfect base-paired double helix with each other.

"Nucleic acid molecule" is a polymer of nucleotides consisting of at least two nucleotides covalently linked together. A nucleic acid molecule can be a polynucleotide or an oligonucleotide. A nucleic acid molecule can be deoxyribonucleic acid (DNA), ribonucleic acid (RNA), or a combination of both. A nucleic acid molecule may comprise methylated nucleotides generated in vivo or by treating with methyltransferases (e.g., dam methyltransferase). A nucleic acid molecule may be single stranded or double stranded, as specified. A double stranded nucleic acid molecule may comprise non-complementary segments.

Nucleic acid molecules generally comprise phosphodiester bonds, although in some cases, they may have alternate backbones, comprising, for example, phosphoramide ((Beaucage and Iyer, 1993) and references therein; (Letsinger and Mungall, 1970); (Sprinzl et al., 1977); (Letsinger et al., 1986); (Sawai, 1984), and (Letsinger et al, 1988)), phosphorothioate ((Mag et al, 1991); and U.S. Pat. No. 5,644,048 (Yau, 1997)), phosphorodithioate(Brill et al., 1989), O-methylphosphoroamidite linkages(Eckstein, 1992), and peptide nucleic acid backbones and linkages ((Egholm et al., 1992); (Meier and Engels, 1992); (Egholm et al, 1993); and (Carlsson et al., 1996)). Other analog nucleic acids include those with bicyclic structures including locked nucleic acids, (Koshkin et al., 1998); positive backbones (Dempcy et al., 1995); non-ionic backbones (U.S. Pat. No. 5,386,023 (Cook and Sanghvi, 1992), U.S. Pat. No. 5,637,684 (Cook et al., 1997), U.S. Pat. No. 5,602,240 (Mesmaeker et al., 1997), U.S. Pat. No. 5,216,141 (Benner, 1993) and U.S. Pat. No. 4,469,863 (Ts'o and Miller, 1984); (von Kiedrowski et al., 1991); (Letsinger et al., 1988), (Jung et al., 1994); (Sanghvi and Cook, 1994); (De Mesmaeker et al., 1994); (Gao and Jeffs, 1994); (Horn et al., 1996)) and non-ribose backbones, including those described in U.S. Pat. No. 5,235,033 (Summerton et al., 1993) and U.S. Pat. No. 5,034,506 (Summerton and Weller, 1991), and (Sanghvi and Cook, 1994). Nucleic acids containing one or more carbocyclic sugars are also included within the definition of nucleic acids (Jenkins and Turner, 1995). Several nucleic acid analogs are described in Rawls, C & E News Jun. 2, 1997 page 35 (RAWLS, 1997).

All methods described herein to be performed on "a nucleic acid molecule", can be applied to a single nucleic acid molecule, or more than one nucleic acid molecules. For example, said methods can apply to many identical nucleic acid molecules, such as PCR copies derived from a single nucleic acid molecule. In another example, said methods can also apply to many nucleic acid molecules of diverse sequences, such as extracted and sheared fragments of genomic DNA molecules. In another example, said methods can also apply to a plurality of groups of nucleic acid molecules, each group comprising copies of a specific nucleic acid molecule, such as the combination of products derived from multiple PCR assays. Examples mentioned above are non-limiting A nucleic acid molecule may be linked to a surface (e.g., functionalized solid support, adaptor-coated beads, primer-coated surfaces, etc.).

Unless stated otherwise, a "nucleic acid molecule" that participates in reactions, or is said to be exposed to conditions or subjected to processes (or other equivalent phrase) to cause a reaction or event to occur, comprises the nucleic acid molecule and everything associated with it (sometimes referred to as "parts" or "surroundings"). Incorporated nucleotides, attached adaptors, hybridized primers or strands, etc, that are associated (e.g., bound, hybridized, attached, incorporated, ligated, etc.) with the nucleic acid molecule prior to or during a method described herein, are or become part of the nucleic acid molecule, and are comprised in the term "nucleic acid molecule". For example, a nucleotide that is incorporated into the nucleic acid molecule in a step becomes part of the nucleic acid molecule in the next steps. For example, an adaptor that is already attached to the nucleic acid molecule prior to being subjected to methods described herein, is part of the nucleic acid molecule.

The term "adaptor" refers to an oligonucleotide or polynucleotide, single-stranded (e g., hairpin adaptor) or double-stranded, comprising at least a part of known sequence. Adaptors may include no sites, or one or more sites for restriction endonuclease recognition, or recognition and cutting. Adaptors may comprise methyltransferase recognition sites. Adaptors may comprise one or more cleavable features or other modifications. Adaptors may or may not be anchored to a surface, and may comprise one or more modifications (for example, to allow anchoring to lipid membranes or other surfaces) and/or be linked to one or more enzymes (e.g. helicases) or other molecules.

A "hairpin adaptor" is an adaptor comprising a single strand with at least a part exhibiting self-complementarity. Such self-complementarity forms a double-stranded structure. Hairpin adaptors may comprise modified nucleotides or other modifications that, for example, enable attachment to surfaces, nicking, restriction enzyme recognition, etc.

The term "polymerization" refers to the process of covalently connecting nucleotides to form a nucleic acid molecule (or a nucleic acid construct), or covalently connecting nucleotides via backbone bonds, one nucleotide at a time, to an existing nucleic acid molecule or a nucleic acid construct. The latter case is also termed "extension by polymerization". Polymerization (extension by polymerization) can be template-dependent or template-independent. In template-dependent polymerization, the produced strand is complementary to another strand which serves as a template during the polymerization reaction, whereas in template-independent polymerization, addition of nucleotides to a strand does not depend on complementarity.

"Template strand": As known by those skilled in the art, the term "template strand" refers to the strand of a nucleic acid molecule that serves as a guide for nucleotide incorporation into the nucleic acid molecule comprising an extendable 3' end, in the event that the nucleic acid molecule is subjected to a template-dependent polymerization reaction. The template strand guides nucleotide incorporation via base-pair complementarity, so that the newly formed strand is complementary to the template strand.

"Extendable 3' end" refers to a free 3' end of a nucleic acid molecule or nucleic acid construct, said 3' end being capable of forming a backbone bond with a nucleotide during template-dependent polymerization. "Extendable strand" is a strand of a nucleic acid molecule that comprises an extendable 3' end.

A "construct" may refer to adaptors (hairpins or others) or other method-made entities such as, for example, anchored oligo- or poly-nucleotides.

"Segment" When referring to nucleic acid molecules, or nucleic acid constructs, "segment" is a part of a nucleic acid molecule (e.g., template strand) or a nucleic acid construct (e.g., adaptor) comprising at least one nucleotide.

The terms "attachment" and "ligation" are used interchangeably, unless otherwise stated or implied by context.

When referring to restriction enzymes, including nicking endonucleases, the terms "recognition site" and "restriction site" are used interchangeably, unless otherwise stated or implied by context, and refer to sites that can be recognized by such enzymes which may cut inside or outside of these sites.

Nucleic Acid Molecules

Nucleic acid molecules can be obtained from several sources using extraction methods known in the art. Examples of sources include, but are not limited to, bodily fluids (such as blood, urine, serum, lymph, saliva, anal and vaginal secretions, perspiration and semen) and tissues (normal or pathological such as tumors) of any organism, including human samples; environmental samples (including, but not limited to, air, agricultural, water and soil samples); research samples (such as PCR products); purified samples, such as purified genomic DNA, RNA, etc. In certain embodiments, genomic DNA is obtained from whole blood or cell preparations from blood or cell cultures. In further embodiments, nucleic acid molecules comprise a subset of whole genomic DNA enriched for transcribed sequences. In further embodiments, the nucleic acid molecules comprise a transcriptome (i e., the set of mRNA or "transcripts" produced in a cell or population of cells) or a methylome (i.e., the population of methylated sites and the pattern of methylation in a genome).

In some embodiments, nucleic acid molecules of interest are genomic DNA molecules. Nucleic acid molecules can be naturally occurring or genetically altered or synthetically prepared. Nucleic acid molecules can be directly isolated without amplification, or isolated by amplification using methods known in the art, including without limitation polymerase chain reaction (PCR), strand displacement amplification (SDA), multiple displacement amplification (MDA), rolling circle amplification (RCA), rolling circle amplification (RCR) and other amplification methodologies. Nucleic acid molecules may also be obtained through cloning, including but not limited to cloning into vehicles such as plasmids, yeast, and bacterial artificial chromosomes.

In some embodiments, the nucleic acid molecules are mRNAs or cDNAs. Isolated mRNA may be reverse transcribed into cDNAs using conventional techniques, as described in Genome Analysis: A Laboratory Manual Series (Vols. I-IV) (Green, 1997) or Molecular Cloning: A Laboratory Manual (Green and Sambrook, 2012).

Genomic DNA is isolated using conventional techniques, for example as disclosed in Molecular Cloning: A Laboratory Manual (Green and Sambrook, 2012). The genomic DNA is then fractionated or fragmented to a desired size by conventional techniques including enzymatic digestion using restriction endonucleases, random enzymatic digestion, or other methods such as shearing or sonication.

Fragment sizes of nucleic acid molecules can vary depending on the source and the library construction methods used. In some embodiments, the fragments are 300 to 600 or 200 to 2000 nucleotides or base pairs in length. In other embodiments, the fragments are less than 200 nucleotides or base pairs in length. In other embodiments, the fragments are more than 2000 nucleotides or base pairs in length.

In a further embodiment, fragments of a particular size or in a particular range of sizes are isolated. Such methods are well known in the art. For example, gel fractionation can be used to produce a population of fragments of a particular size within a range of base pairs, for example for 500 base pairs ±50 base pairs.

In one embodiment, the DNA is denatured after fragmentation to produce single stranded fragments.

In one embodiment, an amplification step can be applied to the population of fragmented nucleic acid molecules. Such amplification methods are well known in the art and include without limitation: polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA) (for circularized fragments), and invasive cleavage technology.

In some embodiments, a controlled random enzymatic ("CoRE") fragmentation method is utilized to prepare fragments (Peters et al., 2012).

Other suitable enzymatic, chemical or photochemical cleavage reactions that may be used to cleave nucleic acid molecules include, but not limited to, those described in WO 07/010251 (Barnes et al., 2007) and U.S. Pat. No. 7,754,429 (Rigatti and Ost, 2010), the contents of which are incorporated herein by reference in their entirety.

In some cases, particularly when it is desired to isolate long fragments (such as fragments from about 150 to about 750 kilobases in length), DNA isolation methods described in U.S. Pat. No. 8,518,640 (Drmanac and Callow, 2013) can be applied.

Restriction Enzymes

In many embodiments, nicking endonucleases are used to generate an extendable 3' end within a nucleic acid molecule, or adaptor, etc. A nicking endonuclease can hydrolyze only one strand of a duplex to produce DNA molecules that are "nicked" rather than cleaved. The nicking can result in a 3'-hydroxyl and a 5'-phosphate. Examples of nicking enzymes include but are not limited to Nt.CviPII, Nb.Bsmi, Nb.BbvCI, Nb.BsrDI, Nb.BtsI, Nt.BsmAI, Nt BspQI, Nt.Alwi, Nt.BbvCI, or Nt.BstNBI. Nicking endonucleases may have non-palindromic recognition sites. Nicking endonucleases are available, for example from New England BioLabs. Some nicking endonucleases may be nicking homing endonucleases such as I-BasI and I-H muI (Landthaler et al., 2006)(Landthaler et al., 2006) Suitable nicking endonucleases are also described in (Walker et al., 1992); (Wang and Hays, 2000); (Higgins et al, 2001), (Morgan et al., 2000); (Xu et al. 2001); (Heiter et al, 2005); (Samuelson et al., 2004), and (Zhu et al., 2004), which are incorporated herein by reference in their entirety for all purposes.

Polymerases

Several polymerizing agents can be used in the polymerization reactions described herein. For example, depending on the nucleic acid molecule, a DNA polymerase, an RNA polymerase, or a reverse transcriptase can be used in template-dependent polymerization reactions. DNA polymerases and their properties are described in detail in (Kornberg and Baker, 2005) For DNA templates, many DNA polymerases are available. DNA polymerases with strand-displacing capability are used in several embodiments.

In some embodiments, thermostable polymerases are used, such as Therminator® (New England Biolabs), ThermoSequenase™ (Amersham) or Taquenasem (ScienTech, St Louis, Mo.).

Useful polymerases can be processive or non-processive. By processive is meant that a DNA polymerase is able to continuously perform incorporation of nucleotides using the same primer, for a substantial length without dissociating from either the extended primer or the template strand or both the extended primer and the template strand. In some embodiments, processive polymerases used herein remain bound to the template during the extension of up to at least 50 nucleotides to about 1.5 kilobases, up to at least about 1 to about 2 kilobases, and in some embodiments at least 5 kb-10 kb, during the polymerization reaction. This is desirable for certain embodiments, for example, where efficient construction of multiple consecutive copies connected to a nucleic acid molecule is performed.

Detailed descriptions of polymerases are found in US 2007/0048748 (Williams et al, 2007), U.S. Pat. No. 6,329,178 (Patel and Loeb, 2001), U.S. Pat. No. 6,602,695 (Patel and Loeb, 2003), U.S. Pat. No. 6,395,524 (Loeb et al., 2002), U.S. Pat. No. 7,981,604 (Quake, 2011), U.S. Pat. No. 7,767,400 (Harris, 2010), U.S. Pat. No. 7,037,687 (Williams et al., 2006), and U.S. Pat. No. 8,486,627 (Ma, 2013) which are incorporated by reference herein.

Ligases

Adaptors and other nucleic acid constructs can be attached to nucleic acid molecules by using ligation Several types of ligases are suitable and used in embodiments. Ligases include, but are not limited to, NAD+-dependent ligases including tRNA ligase, Taq DNA ligase, *Thermus filiformis* DNA ligase, *Escherichia coli* DNA ligase, Tth DNA ligase, *Thermus scotoductus* DNA ligase, thermostable ligase, Ampligase thermostable DNA ligase, VanC-type ligase, 9° N DNA Ligase, Tsp DNA ligase, and novel ligases discovered by bioprospecting. Ligases also include, but are not limited to, ATP-dependent ligases including T4 RNA ligase, T4 DNA ligase, T7 DNA ligase, Pfu DNA ligase, DNA ligase 1, DNA ligase III, DNA ligase IV, and novel ligases including wild-type, mutant isoforms, and genetically engineered variants. There are enzymes with ligase activity such as topoisomerases (Schmidt et al., 1994).

EXAMPLES

Methods described herein may employ conventional techniques and descriptions offieldssuch as organic chemistry, polymertechnology, molecular biology, cell biology, and biochemistry, which are within the skill of the art. Such conventional techniques include, but are not limited to, polymerization, hybridization and ligation. Such conventional techniques and descriptions can be found in standard laboratory manuals such as "Genome Analysis: A Laboratory Manual Series (Vols. I-IV)" (Green, 1997), "PCR Primer. A Laboratory Manual" (Dieffenbach and Dveksler, 2003), "Molecular Cloning: A Laboratory Manual" (Green and Sambrook, 2012), and others (Berg, 2006); (Gait, 1984), (Nelson and Cox, 2012), all of which are herein incorporated in their entirety by reference for all purposes.

All referenced publications (e.g., patents, patent applications, journal articles, books) are included herein in their entirety.

Highly accurate sequencing using error-prone sequencing platforms can be achieved by sequencing DNA constructs each comprising multiple copies of a single original DNA molecule Such DNA constructs can be attached to adaptors appropriate for sequencing using nanopores for example.

Rolling circle amplification (RCA) can generate copies of circular nucleic acid molecules. A circular nucleic acid molecule can be, for example, a single-stranded nucleic acid molecule ligated to a single-stranded adaptor or ligated to itself, or a double-stranded nucleic acid molecule ligated to a double-stranded adaptor or ligated to itself, or a double-stranded DNA molecule comprising strands 101 and 102 and ligated to adaptors 103 and 104, as shown in FIG. 1A. Adaptors 103 and 104 are hairpin adaptors, and can beblunt-ended or comprise overhangs. 103 and 104 may be the same or different. Such a construct is a dumbbell-shaped circular molecule well known to those skilled in the art, and can be subjected to rolling circle amplification, in order to produce multiple copies of the original DNA molecule.

Other examples of circular nucleic acid molecules include genomic DNA fragments, or PCR products, or other DNA molecules or constructs, that are inserted to circular molecules (e.g., plasmids, vectors, synthesized circular DNA; biosyn.com/circular-oligonucleotide aspx). The insertion can be accomplished, for example, by using ligases to ligate the inserts to circular molecules, or by using transposases. Prior to insertion, DNA fragments can be ligated to adaptors comprising transposase recognition sites, or PCR can be performed using primers comprising transposase recognition sites. Use of transposases is well known to those skilled in the art (example protocol is described in lucigen.com/docs/manuals/MA126E-EZ-Tn5-Transposase pdf). Also, circular nucleic acid molecules may be the products of selective genomic circularization, according to a procedure similar to the one described in (Natsoulis et al, 2011); (Myllykangas et al., 2011). Splint ligation can also be used to generate circular nucleic acid molecules (Drmanac et al, 2016).

Figure 1B:
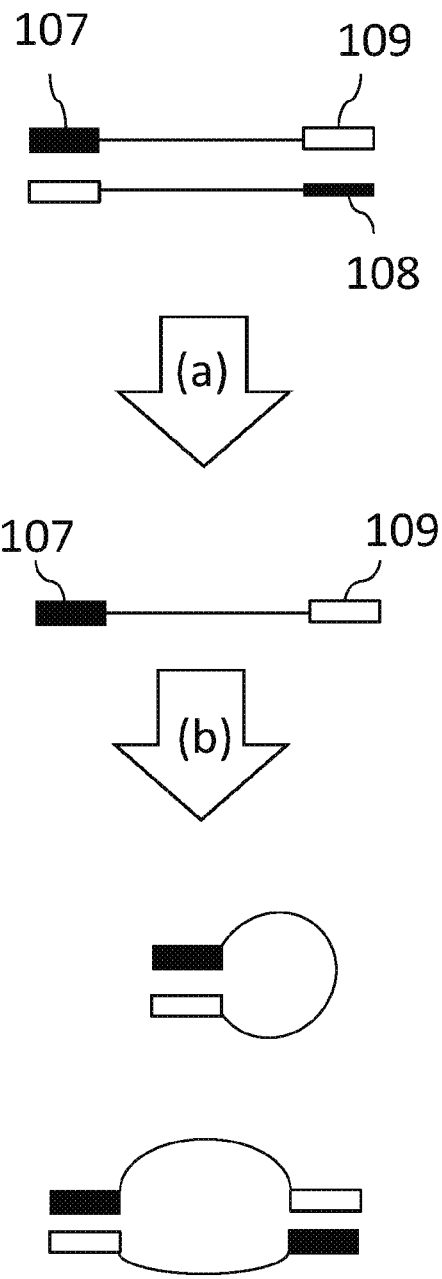
FIG. 1B is a schematic diagram of a method to construct circularized molecules.

In another embodiment shown in FIG. 1B, circular molecules are constructed by first removing one of the two strands of a double-stranded nucleic acid molecule. In particular, a double-stranded nucleic acid molecule is shown which comprises segments 107 and 108 at its 5' ends. 107 and 108 may be parts of adaptors or pans of PCR primers. 107 and 108 are similar, so that 109 (the complement of 108) is at least partially complementary to 107. In some embodiments, the 5' end of 107 is not phosphorylated, whereas the 5' end of 108 is phosphorylated. During step (a), the strand comprising 108 is removed through, for example, enzymatic digestion, leaving the strand comprising 107 and 109 intact. For example, step (a) may comprise incubation with lambda exonuclease which can digest the strand with the phosphorylated 5' end but not the strand with the non-phosphorylated 5' end. During step (b), the remaining strand is allowed to self-anneal, by, for example, raising the temperature to 95° C. and then cooling down. Alternatively, remaining strands anneal to one another. The annealed product in step (b) can be subsequently ligated to a hairpin adaptor, thus creating a circularized molecule.

In other embodiments, 107 and 108 are not similar, 107 is not phosphorylated at its 5' end, whereas 108 is phosphorylated at its 5' end, and the remaining strand in step (a) is self-ligated using a ssDNA-specific ligase (such as CircLigase I or II) to form a circular molecule.

Figure 1C:
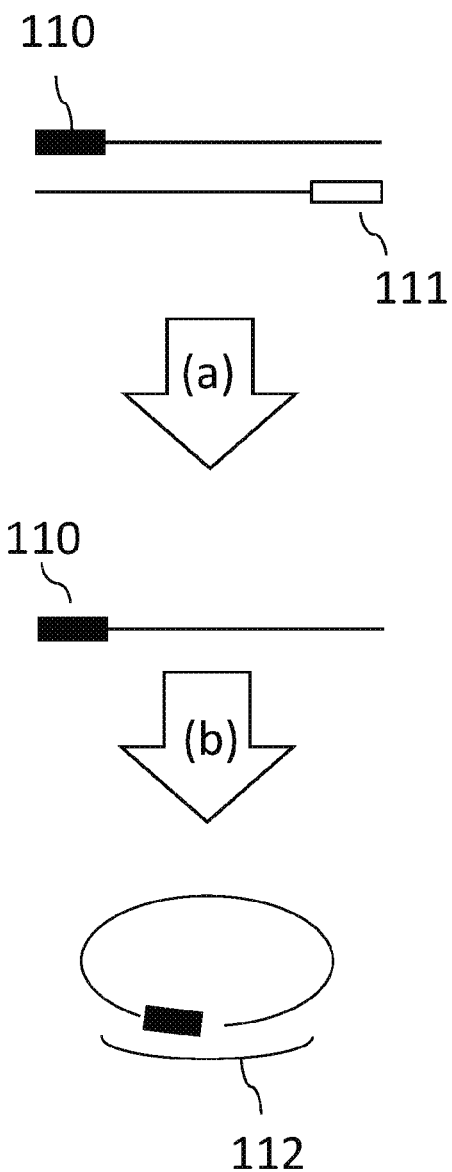
FIG. 1C is a schematic diagram of a method to construct circularized molecules.
Figure 1D:
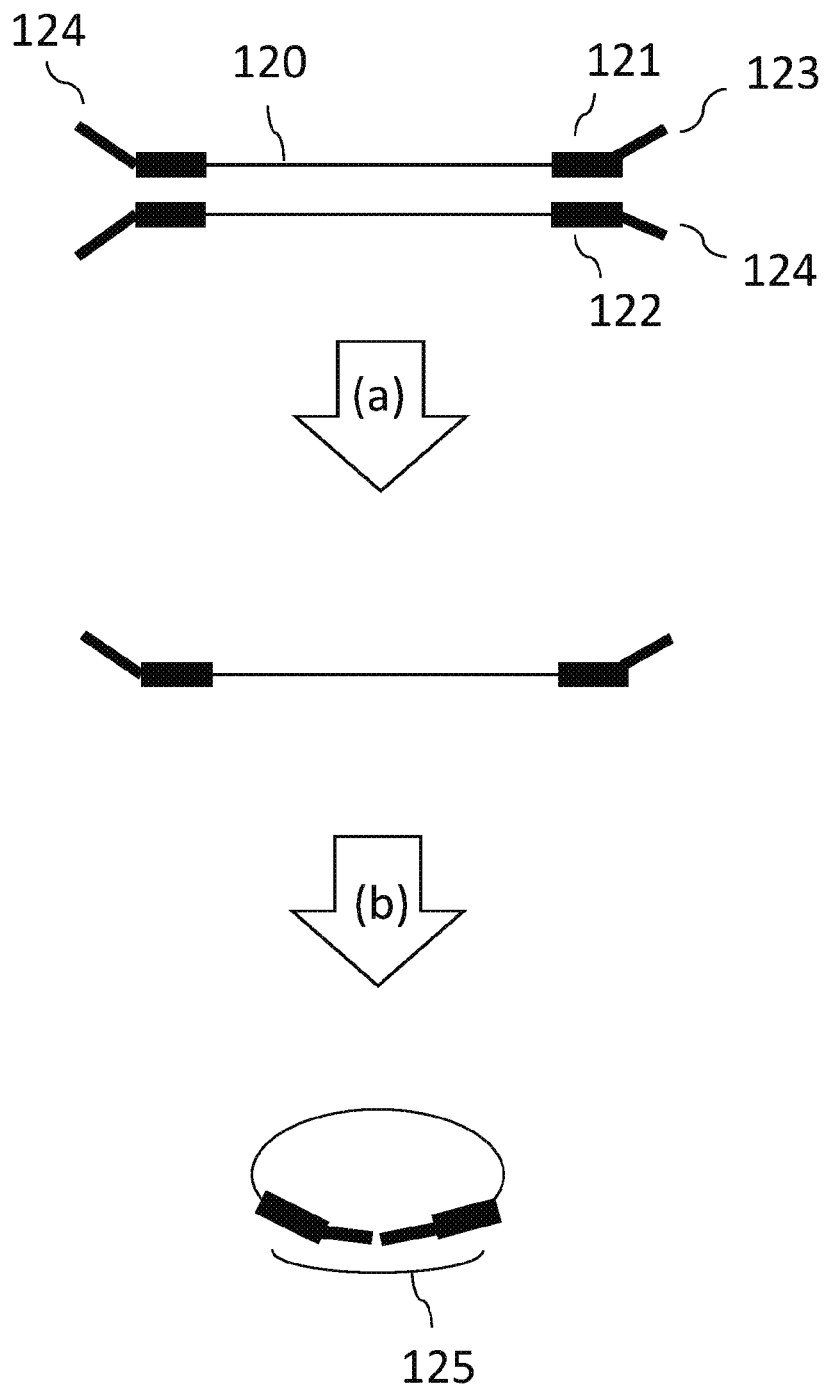
FIG. 1D is a schematic diagram of a method to construct circularized molecules.

In other embodiments, as the ones shown in FIGS. 1C and 1D, a circular molecule can be constructed by splint ligation, wherein a single-stranded nucleic acid molecule can be self-ligated with the help of another single-stranded nucleic acid molecule called the "splint". The splint is at least partially complementary to areas of the nucleic acid molecule to be self-ligated, so that annealing of the splint to the nucleic acid molecule brings its ends close enough to be ligated by a suitable ligase. For example, in the event that both the splint and the nucleic acid molecule are ssDNAs, T4 DNA ligase can be used. In another example, the splint is ssRNA, the nucleic acid molecule is ssDNA, and the suitable ligase is SplintR ligase (New England BioLabs).

In the embodiment shown in FIG. 1C, circular molecules are constructed by first removing one of the two strands of a double-stranded nucleic acid molecule. In particular, a double-stranded nucleic acid molecule is shown which comprises segments 110 and III at its 5' ends. 110 and 111 may be parts of adaptors or parts of PCR primers. In some embodiments, the 5' end of 110 is not phosphorylated, whereas the 5' end of 111 is phosphorylated During step (a), the strand comprising 111 is removed through, for example, enzymatic digestion, leaving the strand comprising 110 intact. For example, step (a) may comprise incubation with lambda exonuclease which can digest the strand with the phosphorylated 5' end but not the strand with the non-phosphorylated 5' end. During step (b), the remaining strand is allowed to anneal to a splint 112 (for example, a ssDNA) which is at least partially complementary to 110 and the area at the 3'-end of the remaining strand from step (a). Annealing to the splint brings the two ends of the remaining strand close so that they can be ligated by a suitable ligase. The annealed product in step (b) can participate in a ligation reaction, thus creating a circularized molecule.

In another embodiment shown in FIG. 1D, a double-stranded nucleic acid molecule 120 is shown (e.g., a genomic DNA fragment, a PCR product; e.g. blunt-ended, dA-tailed) which is ligated to adaptors. In some related embodiments, adaptors comprise two segments 121 and 122 complementary to one another, and two non-complementary segments 123 and 124. During step (a), single strands are produced by, for example, applying heat to denature 120 and its ligated adaptors During step (b), the single strand produced in step (a) is allowed to anneal to a splint 125 (for example, a ssDNA) which is at least partially complementary to the adaptor sequence (e.g., at least part of 123 and at least part of 124). Annealing to the splint brings the two ends of the single strand close so that they can be ligated by a suitable ligase. The annealed product in step (b) can participate in a ligation reaction, thus creating a circularized molecule.

Rolling circle amplification of dumbbell-shaped or circular ssDNA molecules can be initiated by generating priming sites on single-stranded regions of these molecules. Priming sites can be generated by annealing primers or using primases or primase-polymerases (PrimPols)(PICHER and Blanco, 2014). Rolling circle amplification of circular dsDNA molecules can be initiated by introducing, for example, nicks or gaps to generate extendable 3' ends, or by denaturing followed by generating priming sites on resulting single-stranded regions of the denatured molecules.

Figure 1E:
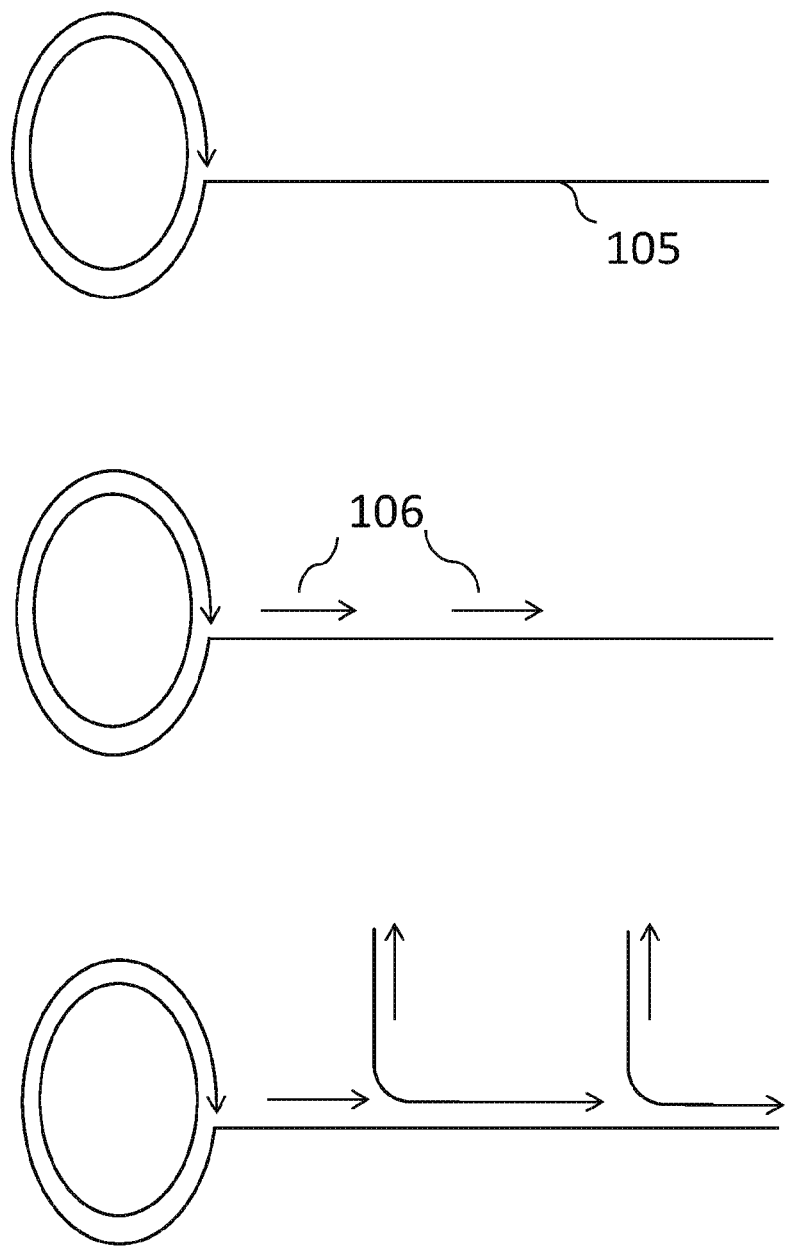
FIG. 1E is a schematic diagram of a method to produce branched constructs.

In the example shown in FIG. 1E, a circular nucleic acid molecule is subjected to rolling-circle amplification. Extension by strand-displacing polymerases displaces strand 105, which becomes a template for primers such as 106 to anneal and provide additional polymerase extension sites, leading to a branched product. Arrowheads show the direction of extension by polymerases.

Branched products such as the one shown in FIG. 1E need to be converted to double-stranded nucleic acid molecules in order to be suitable for sequencing. A method to perform such a conversion is shown in FIGS. 2A and 2B.

Figure 2A:
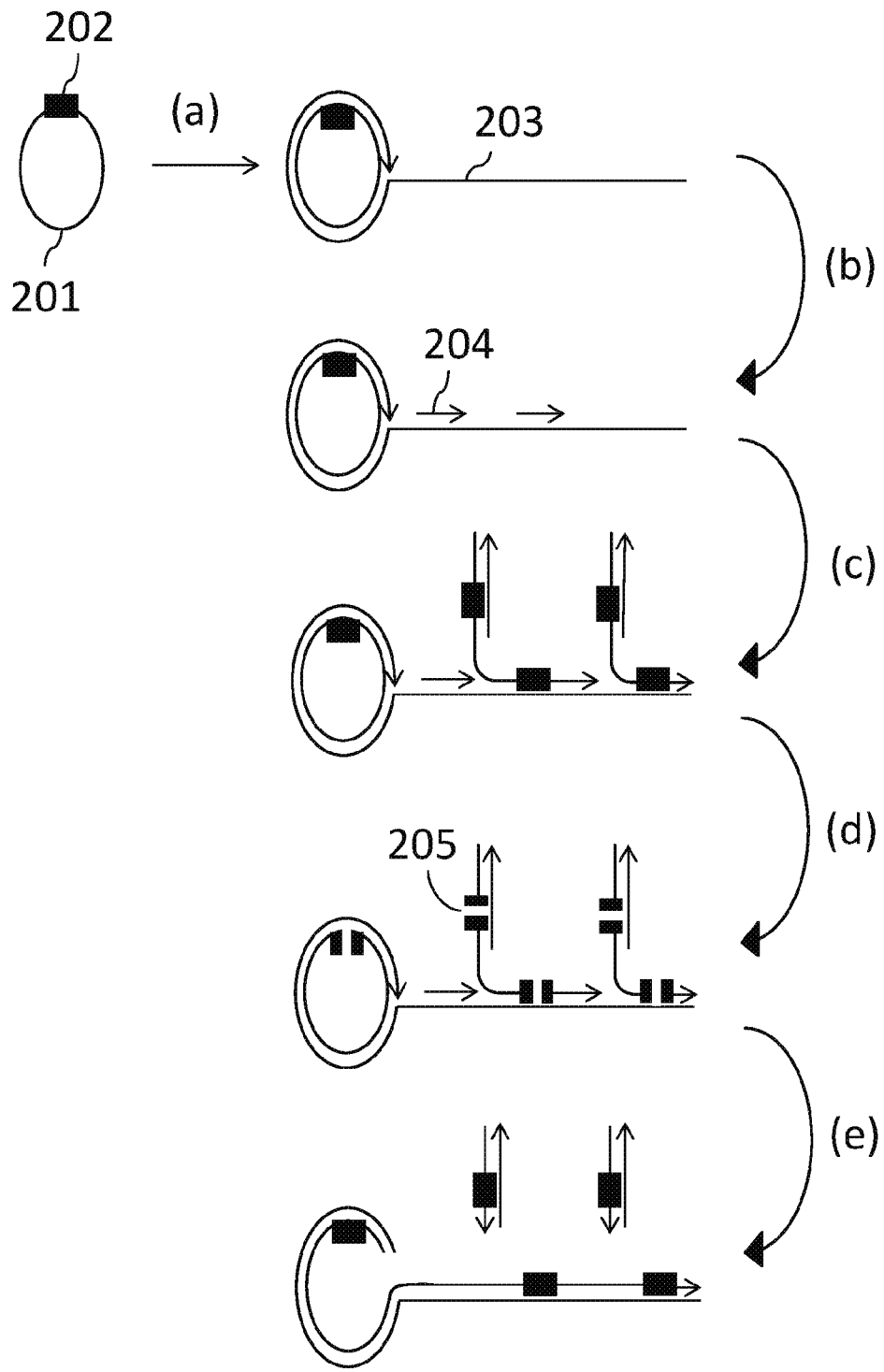
FIG. 2A is a schematic diagram of a debranching method.
Figure 2B:
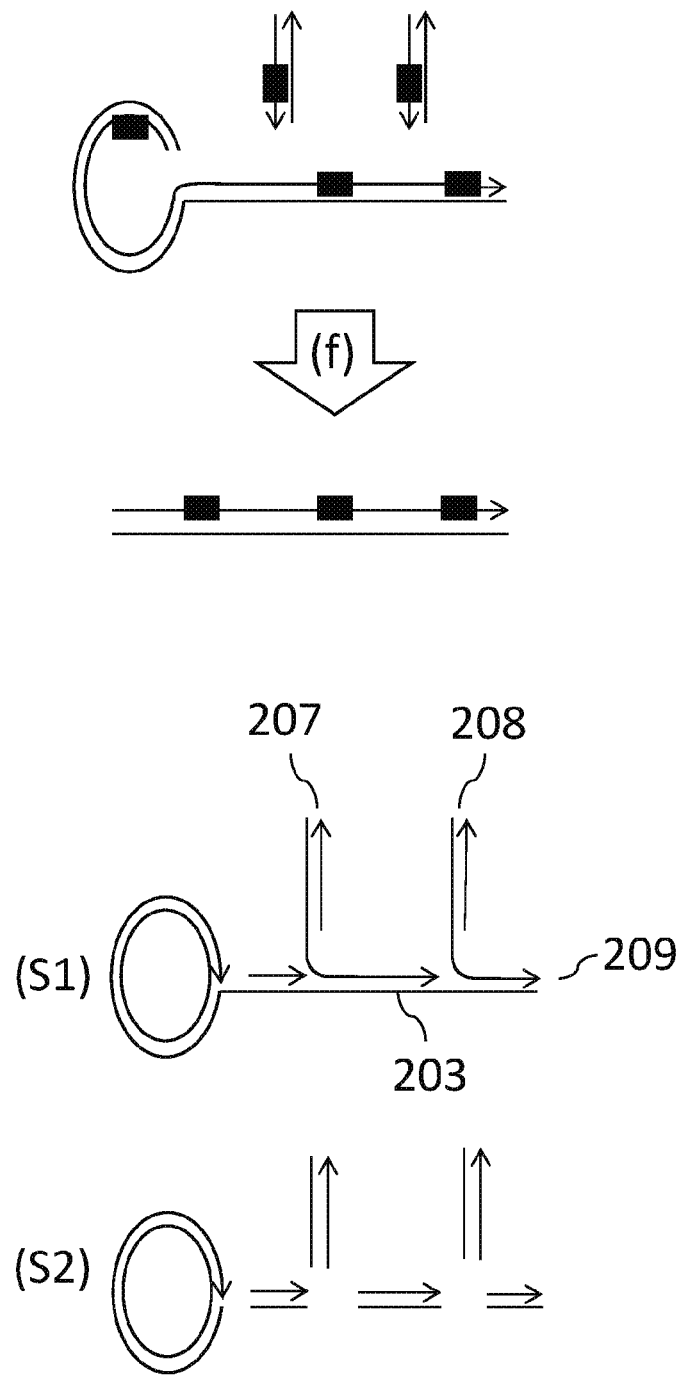
FIG. 2B is a schematic diagram of branched and debranched products.

In some embodiments, a circular ssDNA molecule 201, such as the one shown in FIG. 2A, comprises a nicking site 202 that can be specifically nicked by sequence-specific nicking endonucleases, in the event that the nicking site becomes double-stranded (e.g., in the event that a strand is annealed to at least part of 201, said part comprising 202). The nicking site may be inside or outside or at the beginning or at the end of the nicking endonuclease recognition site of such sequence-specific endonucleases. 201 can be subjected to RCA [steps (a) through (c)]. For example, 201 can be exposed to primers and strand-displacing polymerases such as phi29 DNA polymerase. During step (a), a primer annealed to 201 can be extended by generating a growing strand (203) comprising multiple copies of 201. During step (b), additional primers (such as 204) anneal to 203. Their extension [step (c)] produces a branched product, wherein multiple nicking sites are generated in strand segments comprising sequences that are the same to 202.

During step (d), the RCA constructs generated during steps (a) through (c) are exposed to nicking endonucleases that can nick sites identical to 202, creating nicks such as 205.

The nicks are preferentially created in RCA-generated strand segments comprising copies of 201 with the same sequence with 201, but not to strand segments comprising copies of 201 with sequence complementary to the sequence 201.

During step (e), the 3' ends exposed at the nicks can be extended by using polymerases comprising 5'-3' exonuclease activity and/or flap nuclease activity, such as DNA polymerase I or Taq polymerase. Extension debranches the structure, yielding separate double-stranded nucleic acid molecules. Any remaining nicks can be sealed by a ligase Arrowheads show the direction of extension by polymerases.

The double-stranded molecules generated in step (e) can be optionally further subjected to size selection methods (e.g., AMPure XP selection) before adaptor ligation or after adaptor ligation as part, for example, of a cleanup protocol to get rid of unligated adaptors, to retrieve preferentially long constructs comprising desirable numbers of copies of the original molecule 201, as shown in FIG. 2B, step (f). Subjecting such material to sequencing (for example, adaptor ligation and nanopore sequencing or polymerase-dependent sequencing [e g, Pacific Biosciences sequencers]) can yield preferentially long reads, supporting desired levels of accuracy through consensus sequencing. For example, adaptors carrying anchoring moieties that can attach to surfaces, and helicases or other motor proteins for threading DNA through nanopores can be ligated to double-stranded DNA generated from RCA using the methods described herein. Such adaptors and transposome methods are described in https://nanoporetech.com/rapidsequencing and (Caruccio, 2011). Nanopore sequencing can generate long reads each comprising multiple copies of an original DNA molecule. Such reads can be subjected to Blastn analysis, for example, to identify the copies within each read. Then, the copies within each read can be subjected to multiple alignment analysis (e.g., using Clustal Omega) and consensus sequence building (e.g., cons function of mEMBOSS).

Branched structures (S1) shown in FIG. 2B, that do not undergo debranching as described in FIG. 2A, are problematic for sequencing, because even though they can still ligate to adaptors with their ends 207, 208 and 209, for example, sequencing is expected to produce a lot of undesirable short reads, as short branches cannot be preferentially separated from longer strands (such as 203) in this case.

Debranching approaches have been proposed in the past, involving shearing and/or lengthy protocols requiring purification steps between enzyme incubations (Zhang et al., 2006); (Li et al., 2016a, p. -); (Li et al., 2016b).

Figure 3:
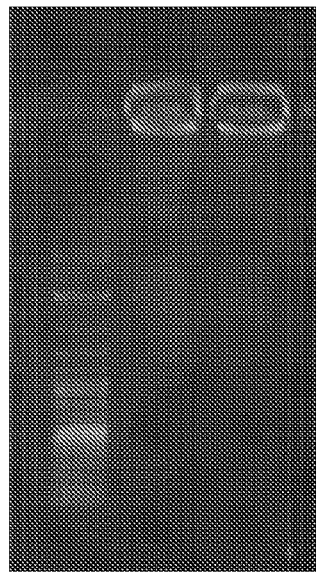
FIG. 3 is an agarose gel electrophoresis visualization of RCA reaction products.

Shearing as a debranching method may be disadvantageous, because it usually requires increased sample volumes, so that samples need to be diluted and re-concentrated, thus increasing the cost of the overall process. Shearing may also be an inefficient method of debranching as shown in FIG. 3. The second lane represents part of a RCA sample with branched material stuck in the gel well. The third lane is part of the same sample that was subjected to shearing using Covaris g-TUBE column. Even though the sample went through 5 rounds of g-TUBE treatment per manufacturer's protocol, no detectable increase in fragmented material was observed.

Debranching methods employing enzymes or other reagents that can indiscriminately cleave at branching points can create mostly undesirable short products such as those shown in (S2), FIG. 2B.

Figure 4:
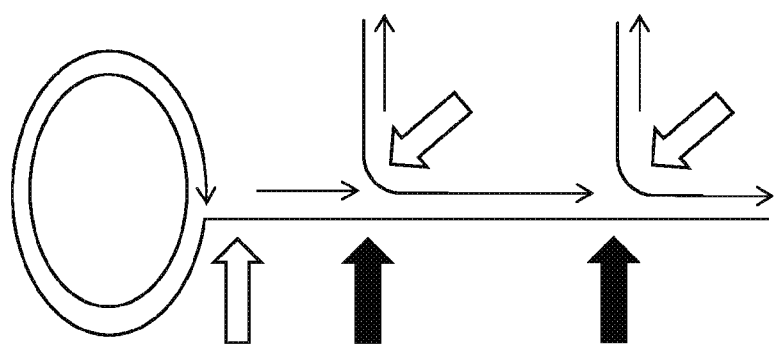
FIG. 4 is a schematic diagram of a branched construct with sites susceptible to nuclease-mediated degradation.

FIG. 4 shows the positions in a branched DNA construct that are susceptible to nucleases such as S1 and MBNase. S1 nuclease can cleave positions pointed by both black and white arrows in FIG. 4, which represent ssDNA areas (white arrows) and positions opposite to nicks or gaps in the double strand (black arrows). Mung bean nuclease can cleave mostly ssDNA areas. These nucleases can be hard to optimize, because they can cut double-stranded regions as well during DNA breathing. S1 nuclease can lead to short fragments because it can cleave at every branch point. Its combination with phi29 polymerase debranching steps was proposed, but such protocols are laborious and anecdotaly reported by others not to improve fragment size and produce only moderate debranching.

Figure 5A:
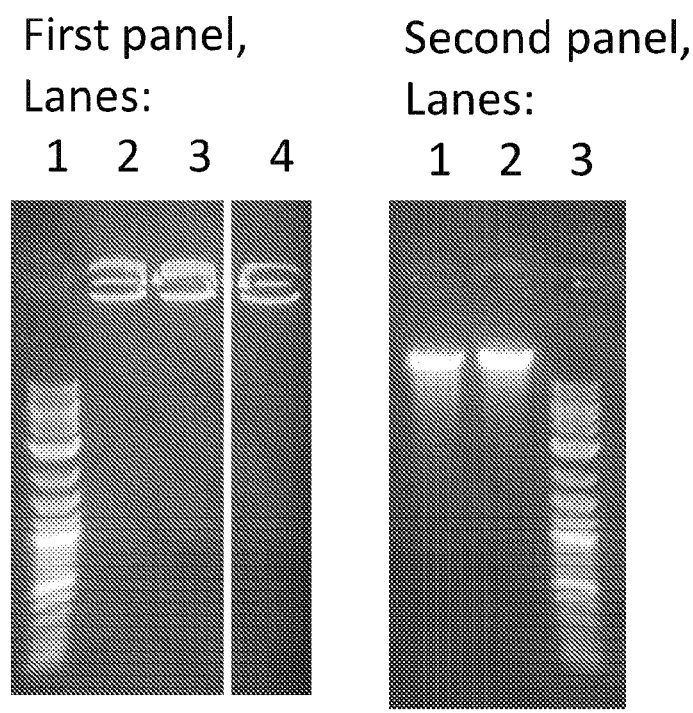
FIG. 5A is an agarose gel electrophoresis visualization of RCA reaction products and controls.

MBNase is known to cut more selectively than S1 nuclease, and spare positions opposite to nicks, potentially leading to longer ssDNA fragments. FIG. 5A shows an experiment of attempted debranching by using MBNase. First panel, lanes 2 and 3, show similar RCA samples treated with 0.5 and 0.25 units respectively of MBNase per µl reaction (37° C., 30 min). Lane 4 shows a similar RCA reaction that remained untreated. There was no noticeable debranching occuring, even though lambda phage genomic DNA samples treated with MBNase under the same conditions showed smears indicative of MBNase-dependent non-specific degradation. Specifically, lanes 1 and 2, second panel, show lambda phage DNA treated with 0.5 and 0.25 units respectively of MBNase per µl reaction. Both lanes contained samples with the same amount of DNA. The smear in lane 1 is more pronounced that the smear in lane 2, consistent with the notion that more MBNase should cause more degradation.

Figure 5B:
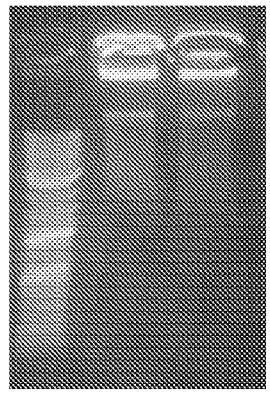
FIG. 5B is an agarose gel electrophoresis visualization of RCA reaction products.

This was an unanticipated result, because there should be some cutting by MBNase, at least at ssDNA segments. In another experiment shown in FIG. 5B, exonuclease III was used in combination with MBNase, to test whether creating gaps at the sites of nicks would promote MBNase digestion by generating larger areas of ssDNA. Lane 2 shows an untreated RCA sample, and lane 3 shows an RCA sample treated with exonuclease III and MBNase. Surprisingly, there was no appearance of lower-sized smear that would indicate MBNase-mediated degradation.

Figure 6A:
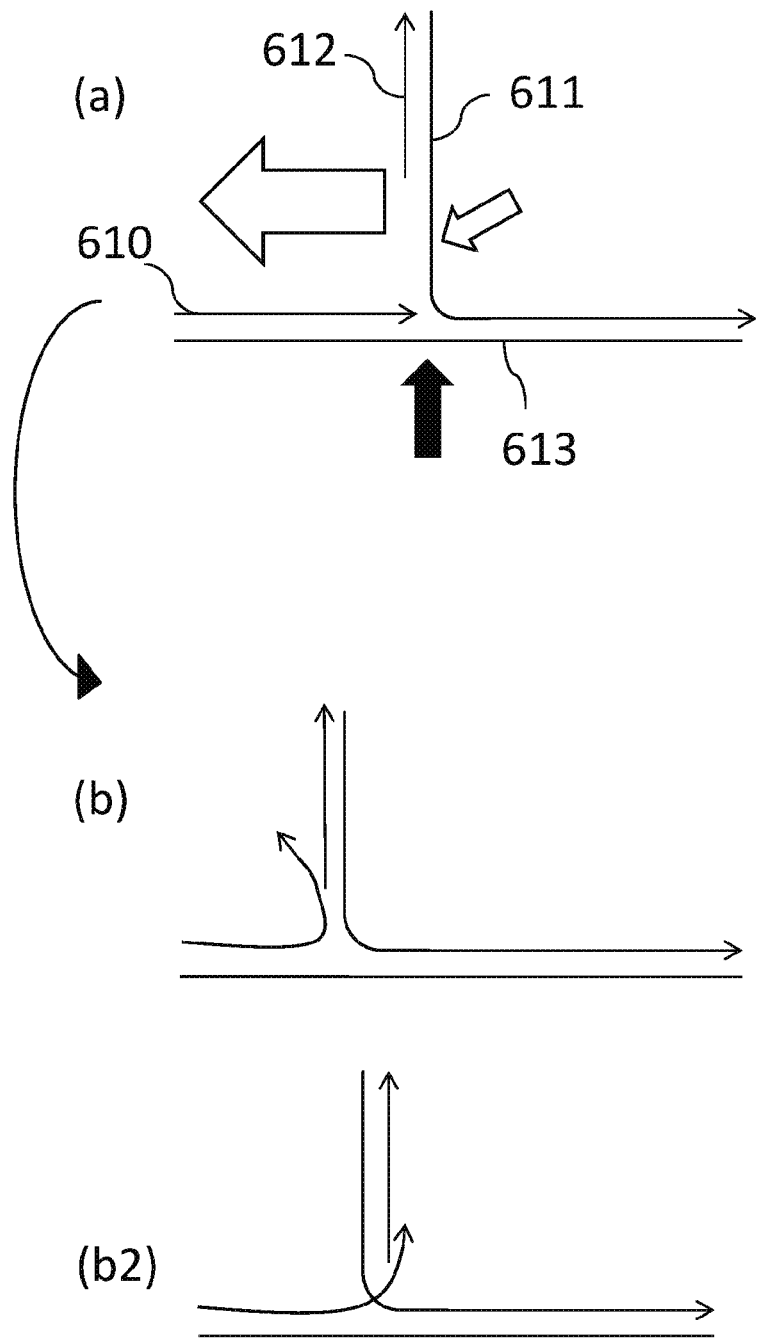
FIG. 6A is a schematic diagram of branched products.

As MBNase I cleaves specifically single-stranded regions, the experimental results suggested that there was no significant presence of single-stranded regions. This can be explained by the mechanism of branch migration, as shown in FIG. 6A, during which the branch comprising part of strand 611 and its complementary strand 612 migrate against the direction of extension of the extending strand 610 (ie towards the direction of the big white arrow). Such branch migration can displace the 3' end of strand 610 and cause reannealing of the single-stranded part of 61l to 613, as shown in (b) and (b2) [(b2) being an alternative representation of (b)], FIG. 6A. Areas susceptible to ssDNA nucleases are pointed by the small white and black arrows; the area pointed by the small white arrow can be cleaved by MBNase I or S1 nuclease, whereas the area pointed by the black arrow can be cleaved by S1 nuclease. Branch migration can cause single-stranded areas (such as the one pointed by the small white arrow) to reanneal, preventing access to nucleases such as MBNase I.

Figure 6B:
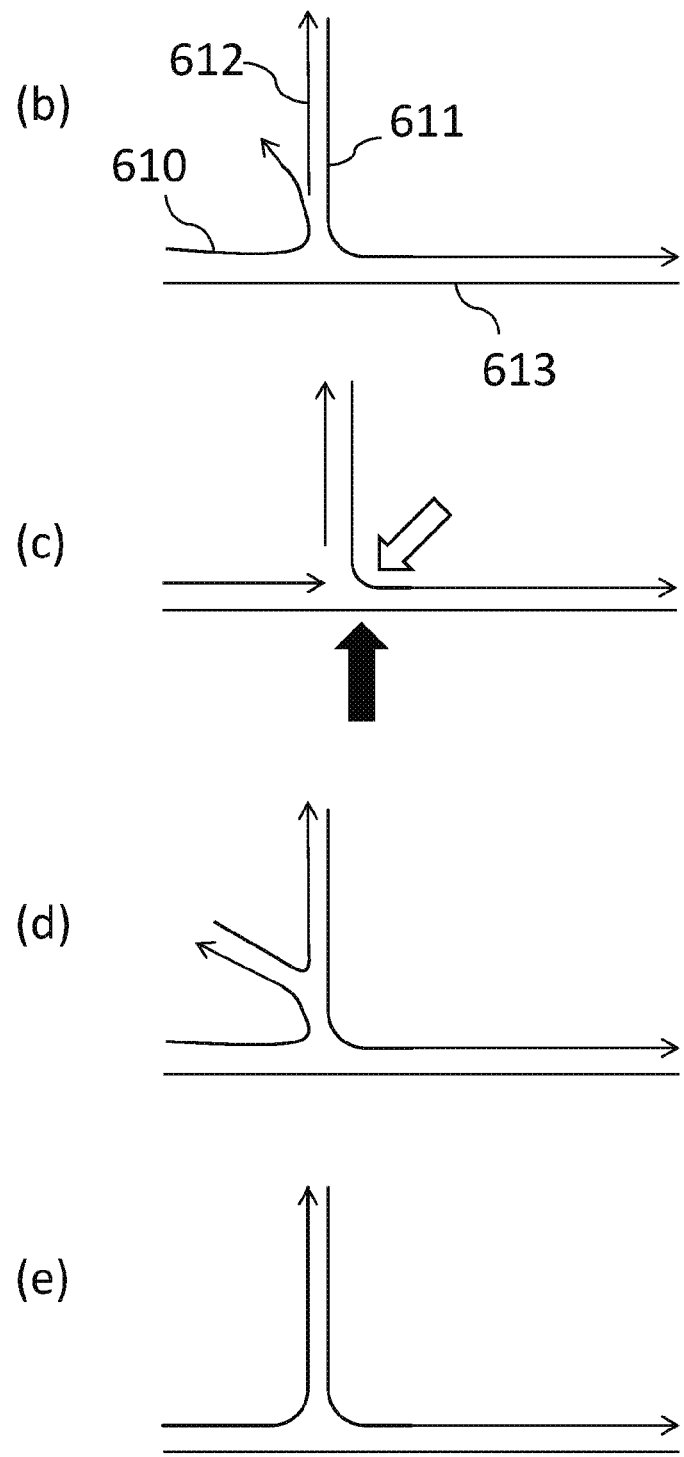
FIG. 6B is a schematic diagram of branched products.

Structures that can arise due to branch migration are shown in FIG. 6B. Structure (c) is a replication fork structure that can occur in RCA or arise from structure (b), in the event that, for example, the displaced 3' end is digested by the 3'-5' exonuclease activity of a strand-displacing polymerase used for RCA (such as phi29 DNA polymerase).

Structure (d) is similar to a Holliday junction and has been described before as the result of replication fork regression. In this structure, part of the 3' end side of 610 anneals to part of the 5' end side of 612.

Structure (e) is a three-way junction which can be formed in the event that the 3' end of 610 can anneal to 611 and extend by displacing 612.

Branch migration is an energetically favorable mode of DNA strand exchange (Lee et al., 1970). Displaced 3' ends such as in (b), FIG. 6A and misprinting events leading to (e), FIG. 6B have been described elsewhere in strand displacement amplification reactions (Lasken and Stockwell, 2007).

Positive torsional stress ahead of a replication fork can cause fork regression, leading to structure (d), FIG. 6B (Postow et al., 2001a); (Postow et al., 2001b). Fork regression can be frequent [>30% of replication forks; (Subramanian and Griffith, 2005)] in complex DNA structures where the DNA ends have difficulty moving freely, or in situations where there are multiple competing replication forks; extensions (Bermejo et al., 2012) as in RCA.

The four-way junction produced by replication fork regression can be processed by cleavage in two opposing strands at the junction point by resolvases (Ishino et al., 2006); (Rass, 2013) such as T7 endonuclease I, GEN1 etc., so that strands such as 613 may be cleaved, leading to short products as described in FIG. 2B, (S2).

Structures such as (d) and (e) do not provide ssDNA regions accessible to MBNase, and may explain the difficulty of MBNase to digest RCA samples. Such structures can be cleaved by resolvases close to the branch points (Dickie et al., 1987).

Replication forks such as (c) in FIG. 6B can be cleaved by resolvases close to positions pointed by the white and black arrows. GEN1 endonuclease (Rass et al., 2010); (Chan and West, 2015) can cleave close to the position pointed by the white arrow, whereas T7 endonuclease I and Mus81-Eme1 endonuclease (Ciccia et al., 2003) can cleave close to the position pointed by the black arrow. Digestion with these endonucleases can lead to debranched products comprising nicks and/or gaps and/or flap structures that can be further repaired/resolved by using polymerases with flap nuclease and/or 5'-3' exonuclease activity. Any nicks can be sealed by ligases.

One challenge with using resolvases endonucleases is that their specificity and cleavage efficiency varies depending on the DNA structure (Chan and West, 2015).

GEN1 cleaves 5'-flaps significantly more efficiently than Holliday junctions. Also, it cannot cleave 3'-flaps. In addition, it may exhibit sequence-specific preferences (Bellendir et al., 2017).

Another disadvantage of using resolvases is that the resolvases need to be removed (via e.g., proteinase treatment and/or purification) prior to adaptor ligation for sequencing.

Another disadvantage is that resolvases may need careful titration. As pointed out by New England BioLabs, it is important to control the amount of enzyme (e.g., T7 endonuclease I) and the reaction time used for cleavage of a particular substrate.

Methods disclosed herein comprise introducing nicks in strand segments within branched structures produced by RCA, in a preferential manner, without nicking the segments complementary to the nicked strand segments.

In some embodiments related to the embodiment in FIG. 2A, 202 is a nicking site of a homing nicking endonuclease. In many embodiments, 201 comprises at least one 202 site, and does not comprise any segments fully complementary to 202. In many embodiments, strand-displacing polymerases are inactivated (e.g., heat-inactivated) before step (d), and nicking enzymes are inactivated (e.g., heat-inactivated) before step (e).

Figure 7:
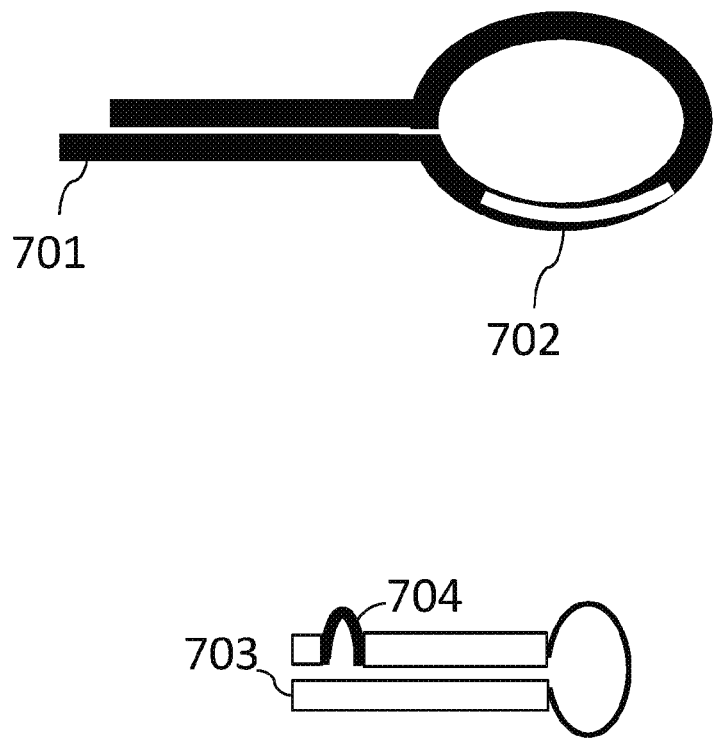
FIG. 7 is a schematic diagram of hairpin adaptors.

In many other embodiments, dumbbell-shaped constructs such as the one shown in FIG. 1A are used as templates for RCA [steps (a) through (c); 2A]. In such embodiments,
hairpin adaptors are used such as those shown in FIG. 7.
In some embodiments, hairpin adaptor 701 is used to create dumbbell-shaped constructs such as the one shown in FIG. 1A. 701 comprises site 702 at least partially residing in its loop, which can be recognized by nicking endonuclease in the event that a strand complementary to said loop is constructed (during RCA for example), rendering the loop double-stranded. In other embodiments, hairpin adaptor 703 is used which comprises a nicking endonuclease recognition site in its stem and a mismatched region 704 within said recognition site, comprising at least one mismatched base. When a strand complementary to the hairpin is constructed during RCA, the mismatch renders only one side of the hairpin's stem recognizable by nicking endonuclease. In other related embodiments, 703 comprises part of a nicking endonuclease recognition site in its stem, preferably with a mismatched region, and upon ligation to a nucleic acid molecule also comprising part of the same recognition site, said recognition site becomes complete.

Figure 8A:
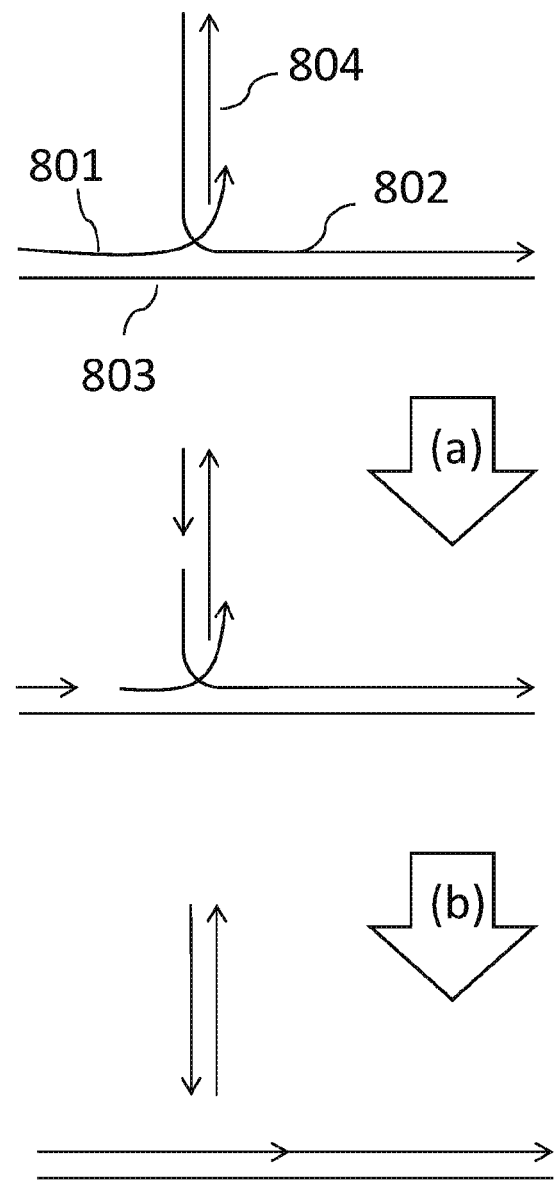
FIGS. 8A through 8C are schematic diagrams of a method for preparing double-stranded copies of nucleic acid molecules.

In some embodiments, nicking endonucleases create nicks in RCA-generated strand segments comprising copies with sequence identical to the sequence of the loop of a hairpin adaptor comprising a nicking site, but not to strand segments comprising copies with sequence complementary to the sequence of the loop of the hairpin adaptor. As shown in FIG. 8A, during step (a), a branched structure is exposed to nicking endonucleases that nick strands 801 and 802, but not their complementary strands 803 and 804. During step (b), the 3' ends exposed at the nicks can be extended by using polymerases comprising 5'-3' exonuclease activity and/or flap endonuclease activity, such as DNA polymerase I or Taq polymerase. Extension debranches the structure, yielding two separate double-stranded nucleic acid molecules. Any remaining nicks can be sealed by a ligase.

Figure 8B:
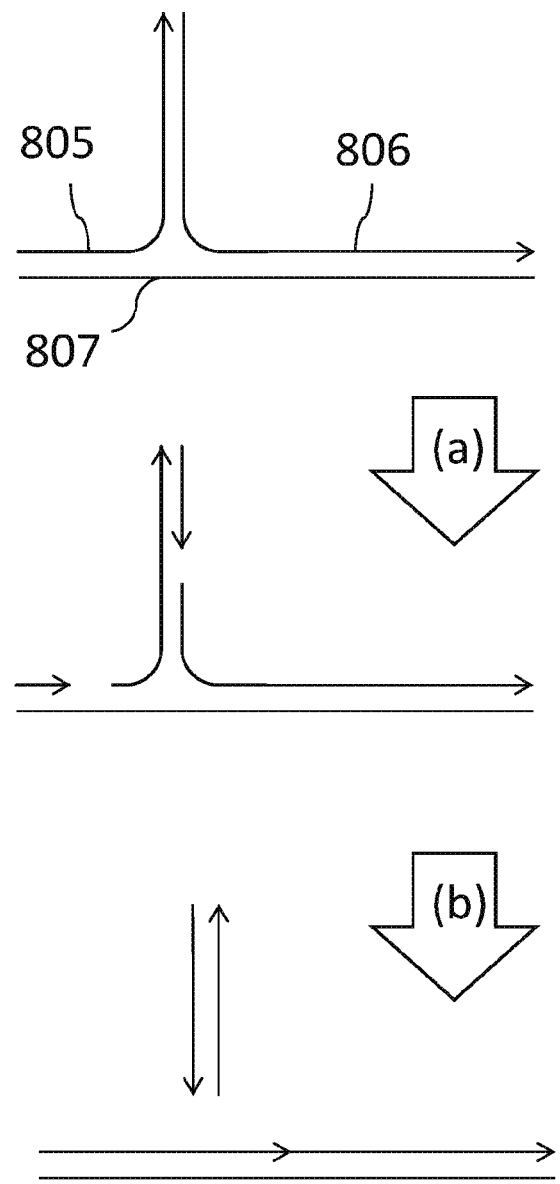

Similarly, in FIG. 8B, the branched structure shown can be exposed to nicking endonucleases nicking 806 and the part of 805 complementary to 807. 807 and the part of 805 complementary to 806 are not nicked.

In other embodiments, nicking endonucleases are used that recognize sites within nucleic acid molecules to be amplified by RCA or whole-genome amplification.

Figure 8C:
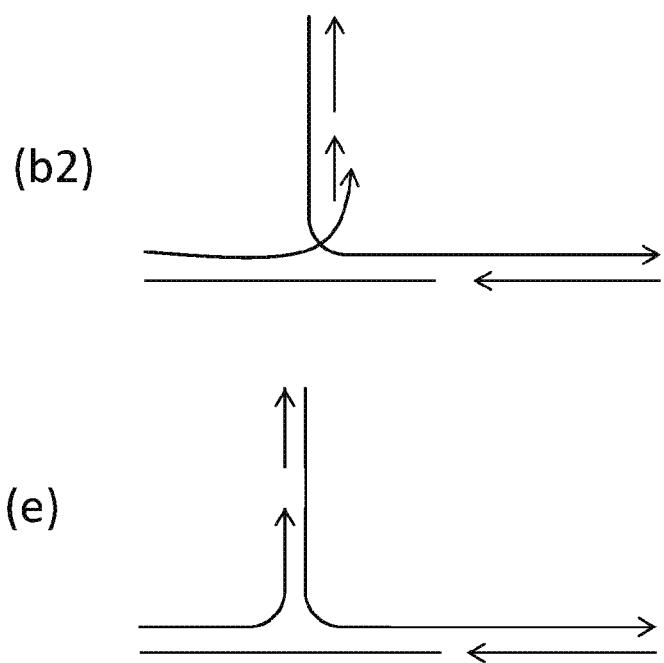

It is important to note that nicking may occur to the opposite strands of what is shown in FIGS. 8A and B, consistent with what is shown in FIG. 8C. In this situation, structure (b2) can be debranched, whereas structure (e) cannot. In some embodiments, nicking with another restriction endonuclease can follow the extension step (b) in FIGS. 8A and B Such restriction endonuclease can recognize the same site with the endonuclease in step (a). FIGS. 8A and B, but nick at the opposite side. For example, in the event that the the first nicking endonuclease is Nt.BbvCI, the other one is Nb BbvCI. The nicking step can be followed by extension and/or ligase steps as described in FIGS. 8A and B.

Alternatively, in some embodiments, resolvases such as T4 endonuclease VII and T7 endonuclease I can be used to resolve branched structures (Rice and Correll, 2008). (Wyatt and West, 2014). Endonucleases have been used before in whole-genome amplification (WGA), but not RCA reactions, for debranching purposes, and without appreciating the complexity of the structures that can arise during strand displacement (Zhang et al., 2006). In fact, these publications consider only structure (a) in FIG. 6A, without taking into account branch migration effects. Also, in those applications, resolvases were used after purification of the WGA material, and not at least partially concurrently with WGA or following WGA by adding resolvases in the same buffer. In addition, DNA polymerase I incubation followed resolvase reaction in (Zhang et al., 2006), but not conducted concurrently.

Figure 8D:
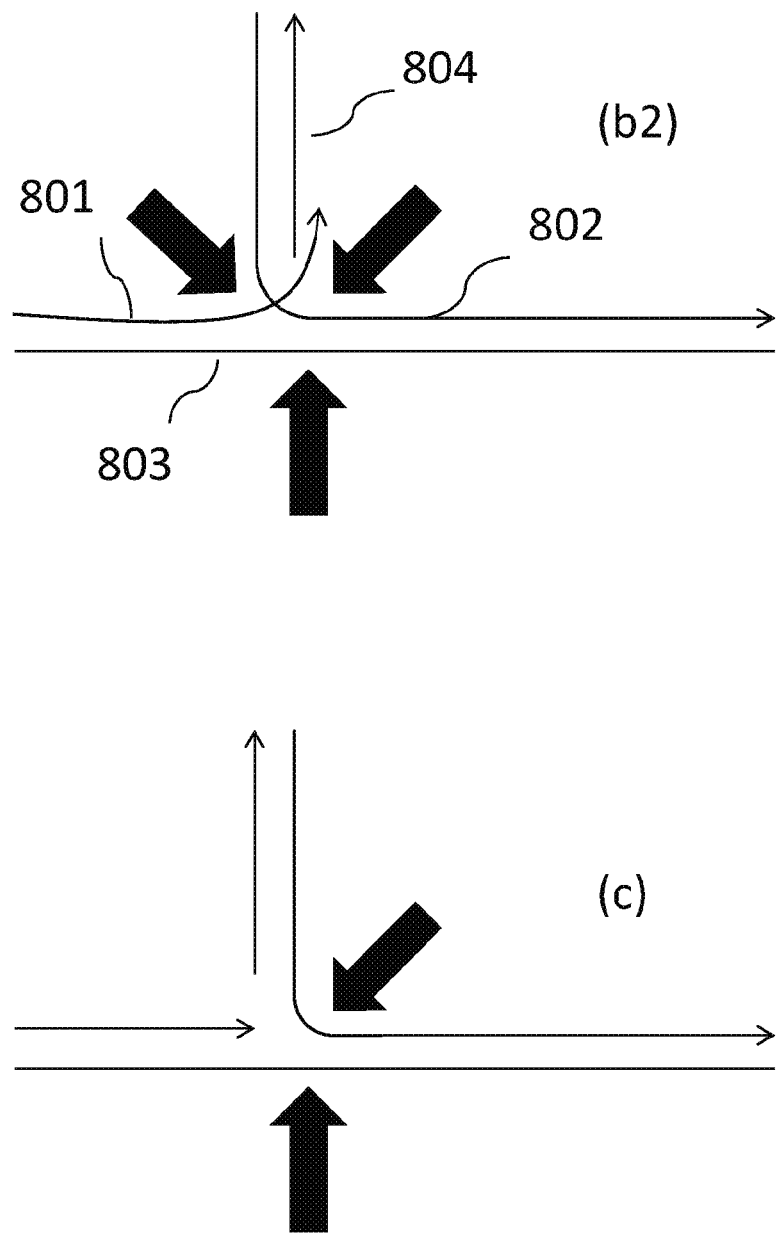
FIG. 8D through 8E are schematic diagrams of branched products with sites susceptible to resolvases.

FIG. 8D shows structures (b2) and (c). Resolvases such as T4 endonuclease VII and T7 endonuclease I cleave at areas around the points indicated by the black arrows. For example, T7 endonuclease I tends to cleave towards the 5' side of a branched point or mispaired region. At each substrate-binding event, resolvases usually cleave at two strands, because of the dimeric nature of such enzymes. Resolvases can nick only once at a time in the event that they are engineered to exist as heterodimers with one active and one inactive subunit (Rice and Correll, 2008). Cleavage of structures (b2) and (c) by resolvases yields shorter products than the nicking-and-extension method described in FIGS. 2A, 2B and 8A.

Figure 8E:
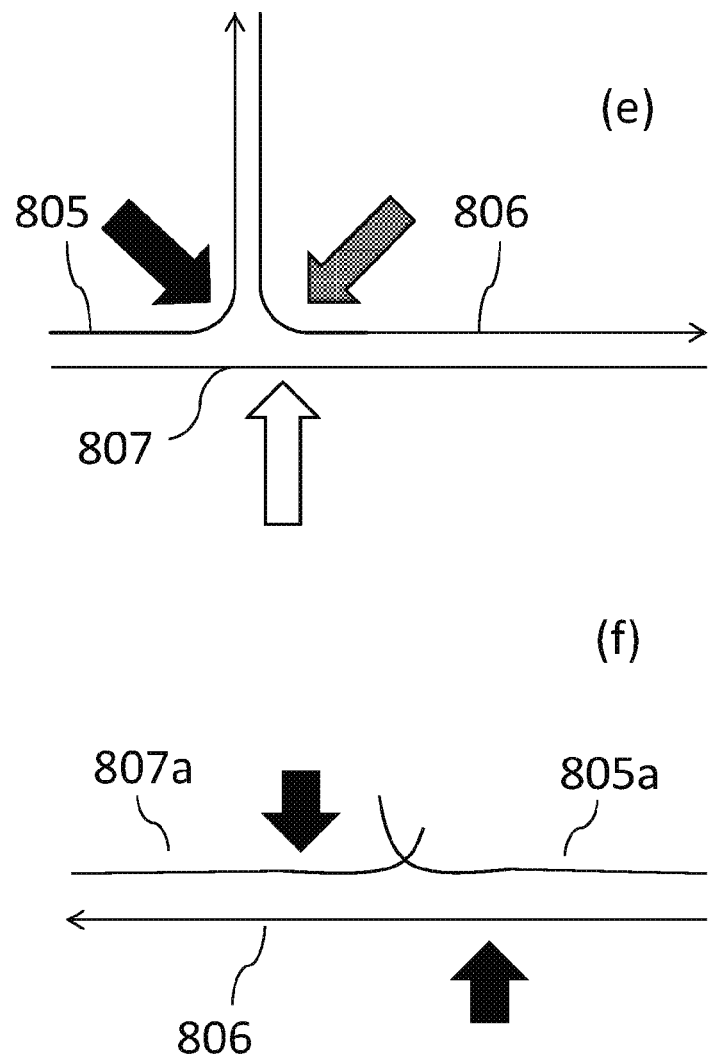

FIG. 8E shows a three-way junction structure (e) with the three arrows (black, white and grey) pointing to potential resolvase cleavage areas (with actual cleavage sites being at the vicinity of the points indicated by said arrows). Such structures are usually cleaved at any two areas indicated by the arrows, in a single substrate-binding event. For example, cleavage at the areas indicated by the black and white arrows creates two products, one comprising part of 805 and its complementary part of 807 (not shown), and the product (f) which comprises 806, 807a (part of 807) and 805a (part of 805). Depending on the locations of the cleavages, product (f) may comprise a nick, gap or flap as shown in FIG. 8E. Such regions of discontinuity or mispairing can be further be recognized and cleaved by resolvases at areas, for example, indicated by the arrows, yielding shorter products. Product (f) can be rescued from further cleavage, by treating with polymerases and/or ligases.

Another important issue about product (f) is that it can be a chimeric product, because during RCA or WGA, strand 806 may be a displaced strand originating from another RCA template, annealed with its 3' end side to 807 and start extending. In contrast, the nicking-and-extension method in FIGS. 8A and B debranches without preserving such chimeric constructs.

Figure 9:
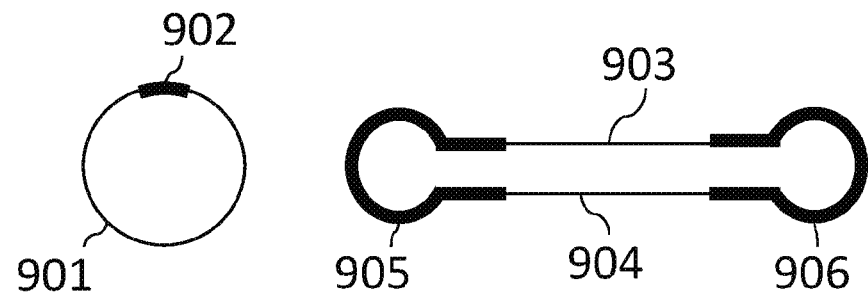
FIG. 9 is a schematic diagram of a debranching method and an agarose gel electrophoresis visualization of a RCA reaction product.
Figure 9:
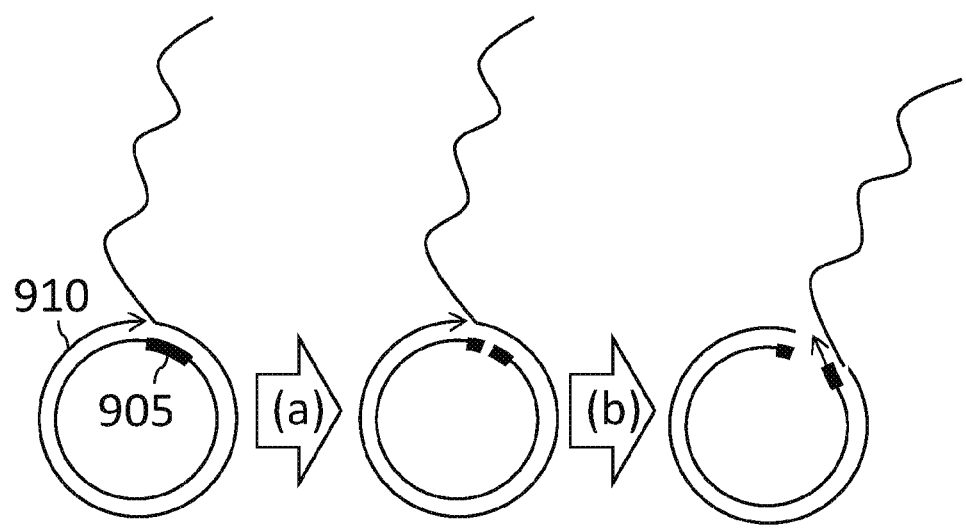
Figure 9:
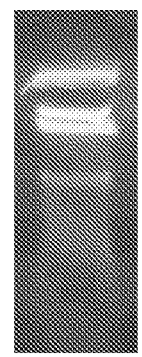
Figure 10:
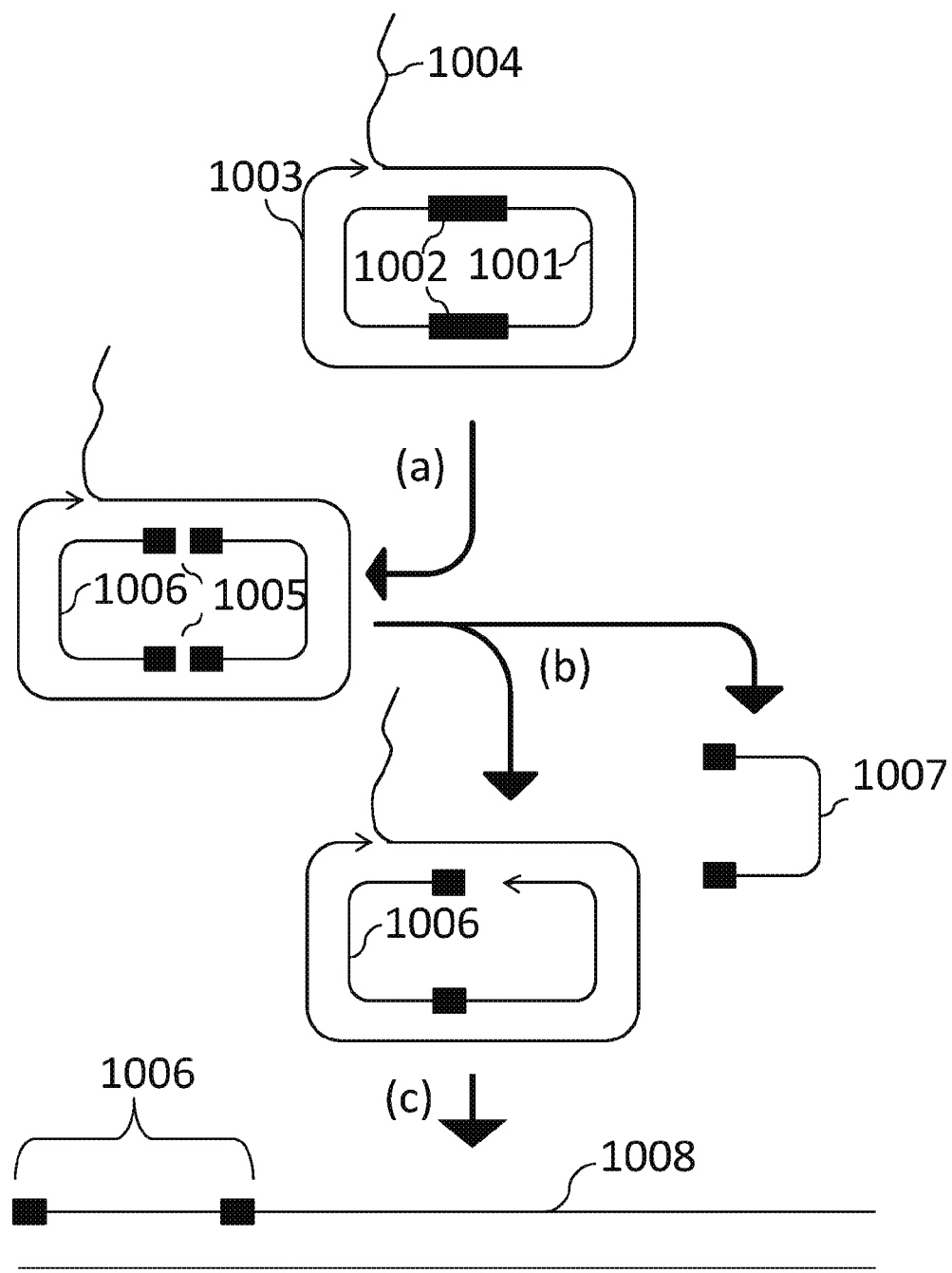
FIG. 10 is a schematic diagram of a debranching method.
Figure 11:
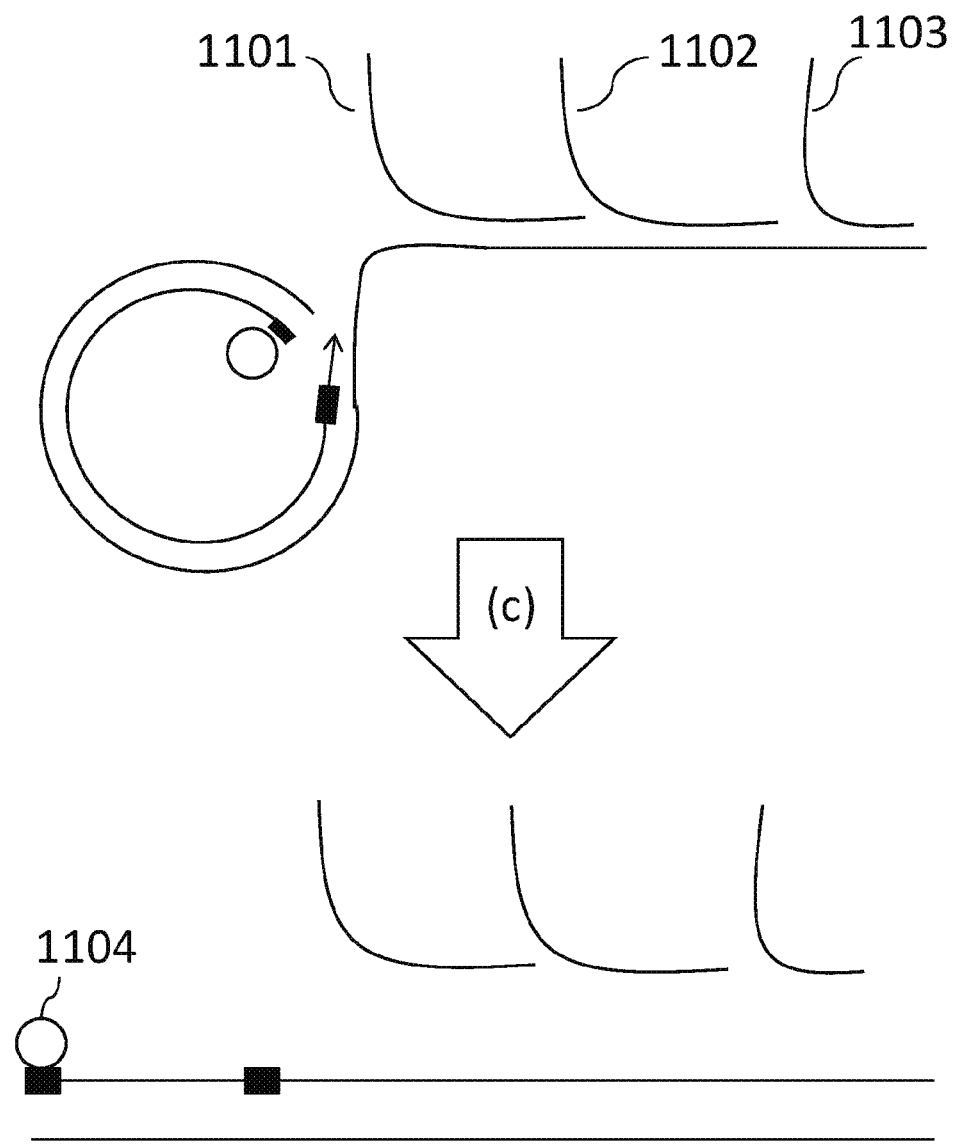
FIG. 11 is a schematic diagram of a debranching method.

In other embodiments, as shown in FIGS. 9 and 10, double-stranded constructs suitable for sequencing can be constructed from rolling-circle amplification products by nickingand extending at least one site on a circular molecule that serves as template for the rolling-circle amplification reaction. A circularized nucleic acid molecule can be, for example, a single-stranded nucleic acid molecule 901 ligated to an adaptor 902, or a double-stranded DNA molecule comprising strands 903 and 904 and ligated to adaptors 905 and 906, as shown in FIG. 9. Adaptors 905 and 906 are hairpin adaptors, and can be blunt-ended or comprise overhangs. 905 and 906 may be the same or different. Circular molecules that can be used, and methods of their construction, are also described in FIGS. 1A through 1D. All of these types of circular constructs are well known to those skilled in the art, and can be subjected to rolling circle amplification, in order to produce multiple copies of the original DNA molecule. The product of rolling circle amplification is a single-stranded molecule, which needs to be converted to a double-stranded structure in order to be suitable for certain sequencing protocols, including nanopore sequencing.

In one embodiment shown in FIG. 9, the circular molecule comprising adaptor 905 is subjected to rolling circle amplification, with the extending strand 910 being extended at the direction of the arrow. In this embodiment, adaptor 905 comprises a feature that can lead to cleavage of the circular molecule. For example, the feature can be one or more cleavable nucleotides, or one or more nicking endonuclease recognition sites (nicking restriction sites), or combinations thereof. In one embodiment, 905 comprises a ribonucleotide which is cleaved by RNase H2 at its 5' end to produce a nick. Polymerases with reverse transcriptase and strand-displacing activities, such as Bst DNA polymerase, can be used for rolling circle amplification of a template that comprises ribonucleotides. In another embodiment, 905 comprises a nicking restriction site which is recognized by a nicking endonuclease which creates a nick in the circular molecule, within or outside adaptor 905. For example, during step (a), a reagent is added to the rolling circle amplification reaction solution to recognize the feature in 905 and cleave the circular molecule. Extension of 910 stops at the site of cleavage, whereas the newly generated 3' end in the cleaved circular molecule is extended by the polymerases added subsequently or already in the reaction solution to convert 910 to a double-stranded structure.

In another embodiment, 905 comprises uracil (dIU) which can be excised by UDG. The resulting abasic site can be cleaved by, for example, treatment with endonuclease VIII. Endonuclease VIII cleaves by leaving a phospho-3'-end, which can be further treated with a phosphatase such as rSAP to remove the phosphate and render the 3'-end extendable. The phosphorylated 3'-end may also be removed by an exonuclease or a polymerase with inherent 3'-5' exonuclease activity, such as phi29 polymerase. Excision and cleavage of dU can be conveniently done with the USER enzyme (New England BioLabs).

In some embodiments, the nucleic acid molecule to be copied comprises cleavable features. For example, the nucleic acid molecule to be copied can be an amplicon that is a product of a PCR reaction comprising cleavable nucleotides such as ribonucleotides or dUTP. Polymerases such as Therminator can be used to carry out such amplification reactions. Taq polymerase, for example, can be used when a PCR reaction comprises dUTP andior primers comprising uracil (dU). Polymerases that can use templates comprising ribonucleotides or dU can be used to carry out rolling circle amplification. For example, Bst polymerase has reverse transcriptase activity. Also, a mixture of polymerases comprising at least one type of polymerase having reverse transcriptase activity can be used. For example, phi29 polymerase can be used together with Klenow exo (-) which has reverse transcriptase activity, or together with a reverse transcriptase.

In one example, lambda phage genomic DNA was subjected to PCR comprising Taq polymerase, a forward primer and a reverse primer comprising a single dU site. The PCR product was subjected to ligation to hairpin adaptors comprising dT overhangs, thereby creating circular molecules. The circular molecules were subjected to rolling-circle amplification with phi29 polymerase, shown in the agarose gel electrophoresis image of FIG. 9. The robust production of high-molecular weight product indicates that phi29 polymerase can readily extend when it encounters dU on the template strand.

The method shown in FIG. 9 can be easily generalized to include embodiments wherein either at least one adaptor or the nucleic acid to be copied or both comprise at least one cleavable feature.

For example, FIG. 10 shows the case of a circular molecule 1001 comprising two adaptors (1002), serving as the template for rolling circle amplification. 1003 is the growing strand extending at the direction of the arrow while displacing its part 1004.

During step (a), 1001 and its surroundings are exposed to nicking endonucleases that recognize restriction sites within the adaptors 1002 and generate nicks (1005), thus generating 1006 and 1007 which are parts of 1001.

During step (b), strand-displacing polymemses may initiate extension at the 3' end of 1006, thus displacing 1007.

During step (c), extensions of both 1003 and 1006 are completed, generating a double-stranded construct 1008 which comprises 1006, as shown.

Cleavable nucleotides and appropriate enzymes and other reagents for cleavage are described in PCT/US2015/027686 (Tsavachidou, 2015).

As described in FIG. 1E and elsewhere herein, rolling-circle amplification typically produces branched products. FIG. 1*l* shows a construct similar to the ones in FIGS. 9 and 10 that has already gone through steps (a) and (b). As shown, the strand displaced during rolling-circle amplification has other strands, such as 1101, 1102 and 1103, annealed to it, forming a branch structure. During step (c), complete extension towards the direction of the arrow displaces 1101, 1102 and 1103. In order to selectively obtain the desirable double-stranded product and not the displaced 1101, 1102 and 1103 strands, one or more capturing features (1104) may be comprised in the circular molecule that served as a template for the rolling-circle amplification reaction. A capturing feature can be a moiety that can facilitate selective purification, for example. In one example, the capturing feature can be a biotinylated nucleotide anywhere within the circular molecule (e.g., within the adaptor, or within the non-adaptor part, in the event, for example, that the circular molecule comprises a strand of a product of a PCR comprising biotinylated nucleotides). Such biotinylated nucleotide can be readily captured, for example, by streptavidin-coated magnetic beads, thus selectively separating the desirable double-standed construct from other strands 1104 may comprise PC-biotin, for example, which is photocleavable, to facilitate easy release of the captured double-stranded construct from the streptavidin-coated substrate, without disturbing (denaturing) the double-stranded construct. Other cleavable capturing features can also be used. Polymerases such as phi29 can readily read through biotinylated nucleotides in the template, as evidenced by the fact that, for example, phi29 polymerase can participate in rolling circle amplification reactions comprising biotin-dUTP (Mullenix et al., 2002).

Example 1

Figure 12:
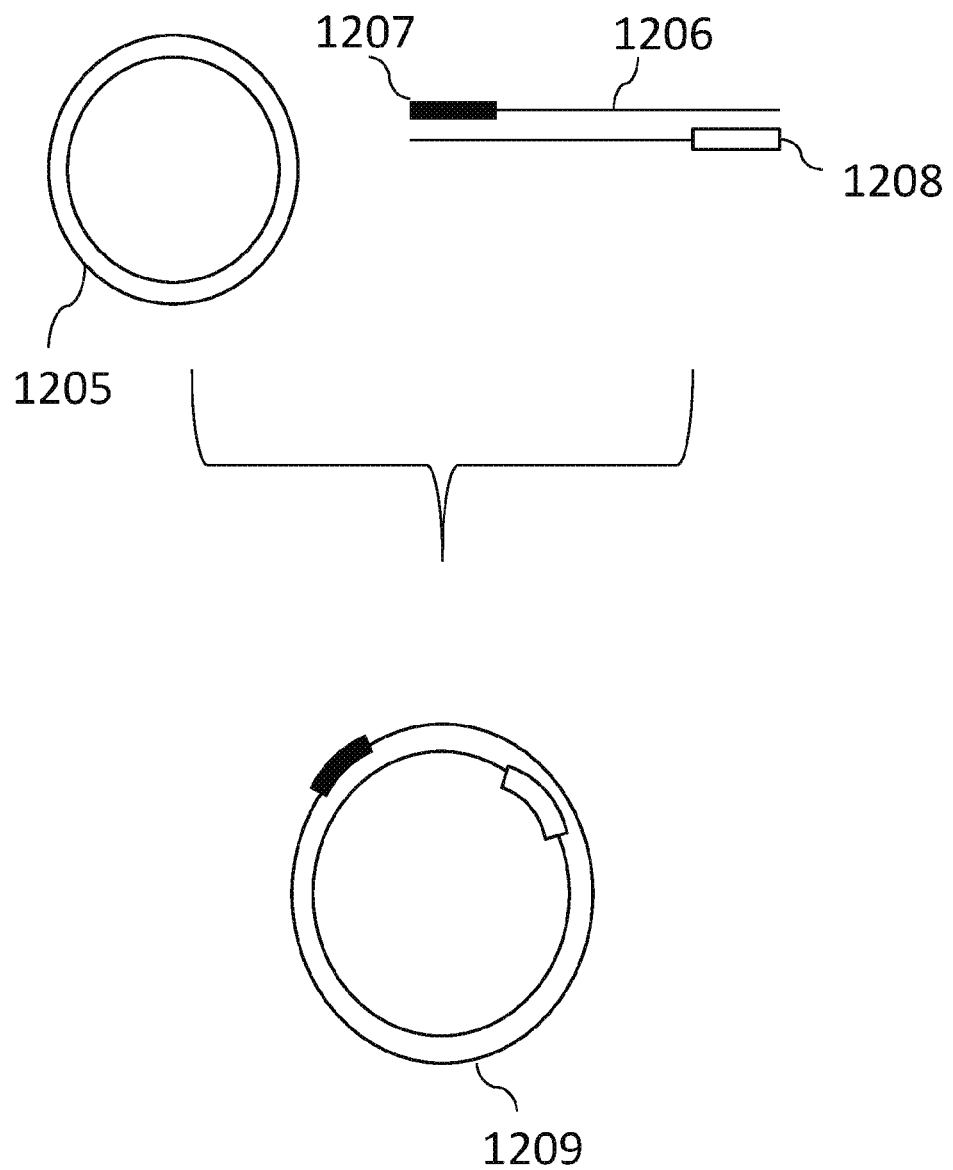
FIG. 12 is a schematic diagram of a method to circularize nucleic acid molecules.
Figure 13:
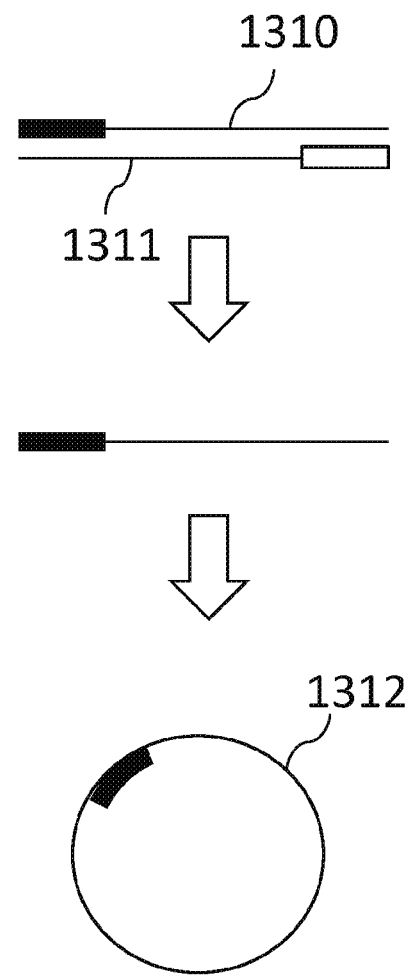
FIG. 13 is a schematic diagram of a method to circularize nucleic acid molecules.

Generating circular nucleic acid molecules:

FIGS. 12 and 13 show circular molecules, in addition to the ones shown in FIGS. 1A through D. In FIG. 12, 1209 can be generated by inserting dsDNA molecule 1206 into 1205, by using transposases, for example. In one embodiment, 1206 is a PCR product produced by using primers 1207 (black rectangle) and 1208 (white rectangle). In another embodiment, 1206 is a DNA fragment ligated to adaptors comprising segments 1207 and 1208. 1207 and 1208 may comprise transposase recognition sequences. 1207 may comprise a nicking endonuclease recognition site to produce a nick in 1209 with an extendable 3' end suitable to initiate RCA. Being able to produce an extendable 3' end within insert 1206 but not 1205 allows initiating RCA in 1209 constructs and prevents undesirable 1205 without insert from participating in RCA 1208 may comprise a nicking endonuclease recognition site to participate in the nicking step (d) of FIG. 2A, thus promoting debranching. In other embodiments, the nicking endonuclease recognition site to be used in step (d) can be present anywhere within 1209.

In many embodiments, a nicking endonuclease recognition site for the purposes of initiating RCA or performing debranching starting with the nicking step (d) (FIG. 2A) may be present anywhere within 1206.

It is preferred that, in the event that there is more than one nicking endonuclease recognition sites within 1209 to participate in step (d) in FIG. 2A, such nicking recognition sites are oriented so that nicks occur in the same strand and not in both strands of 1209.

In other embodiments, circular ssDNA constructs such as 1312 shown in FIG. 13 are used as templates for RCA [steps (a) through (c); FIG. 2A] 1312 can be produced, for example, by a dsDNA molecule comprising strands 1310 and 1311, which yields a single strand 1310 (by using, for example, denaturation or exonuclease-mediated digestion), that can self-ligate by using ligases such as CircLigase (Epicentre) or splint ligation, as described in elsewhere herein. The dsDNA molecule may be a PCR product produced by using primers depicted by a black and a white rectangle. In another embodiment, the dsDNA molecule is a DNA fragment ligated to adaptors. One of the primers or one of the adaptors in such as dsDNA molecule may comprise a nicking endonuclease recognition site to participate in step (d), FIG. 2A. In other embodiments, such a nicking endonuclease recognition site may be present anywhere within 1312, so that a nick can be produced during step (d), FIG. 2A, either in 1312 or its complementary strand produced during RCA. It is preferred that, in the event that there is more than one nicking endonuclease recognition sites in 1312, such nicking recognition sites are oriented so that nicks during step (d) occur either in 1312 or its complementary strand, but not both.

Example 2

Debranching experiment using hairpin dimer construct:
A 20 µl solution comprising 2 µl CutSmart 10× buffer and 4 µl blunt-ended hairpin adaptor (100 µM) with sequence:

```
SEQ. ID. 1:
/5Phos/CTC ACA CAC TTT TTT TGA GAG AGA GAG AGA

GAG AGA TTT CCT CAG CTT TTG TGT GTG AG
``` was incubated at 95° C. for 2 min to denature the adaptor, and then left to cool down at room temperature to promote self-annealing of the hairpin adaptor. 20 µl Quick Ligase Buffer 2× and 2 µl Quick Ligase (New England BioLabs) were added to the hairpin adaptor solution, and incubated at 25° C. for 2 hours to produce circular constructs (hairpin dimers) and then at 65° C. for 10 min to inactivate the ligase.

Rolling circle amplification (RCA): A 40 µl reaction comprising 4 µl CutSmart 10× buffer (New England BioLabs), 2 µl ligation reaction comprising circular constructs (hairpin dimers), 1 µl dNTP (25 mM each), 1 µl PrimPol (Sygnis; Expedeon) and 1 µl phi29 DNA polymerase (~100 units) (Sygnis; Expedeon) was incubated at 30° C. for 1 hour and then at 65° C. for 10 min.

A 10 µl aliquot of the RCA was added 1 µl T7 endonuclease I (10 units; New England BioLabs) and incubated at 37° C. for 1 hour. The reaction was run on a 1% agarose gel (see FIG. 14, 1$^{st}$ Gel, lane 1: marker; lane 2: T7 endonuclease I-treated sample).

Another 10 µl aliquot was added 1 µl Nt.BbvCI (10 units; New England BioLabs) and incubated at 37° C. for 1 hour, then at 80° C. for 20 min to inactivate the nicking enzyme. 20 µl comprising 2 µl ThermoPol II 10× (New England BioLabs), 0.5 µl dNTP (25 mM each) and 0.5 µl Taq polymerase (5 units; New England BioLabs) were added to the reaction and incubated at 68° C. for 1 hour. Then, 3 µl Nb BbvCI (30 units; New England BioLabs) was added, and the reaction was incubated at 37° C. for 1 hour, then at 80° C. for 20 min to inactivate the nicking enzymes, and finally at 68° C. for 1 hour for a final extension step by Taq polymerase. The reaction was then ready for ligation to adaptors to perform nanopore sequencing. One major advantage of this method is that it is a single-tube protocol, not requiring purifications between enzymatic reactions.

Another 10 µl aliquot of the RCA reaction served as a negative control, and was incubated at 37° C. for 1 hour, then at 80° C. for 20 min, but without the addition of nicking enzyme Subsequently, it was added 20 µl of Taq polymerase reaction as described above, but not Nb.BbvCI, and incubated as indicated.

Figure 14:
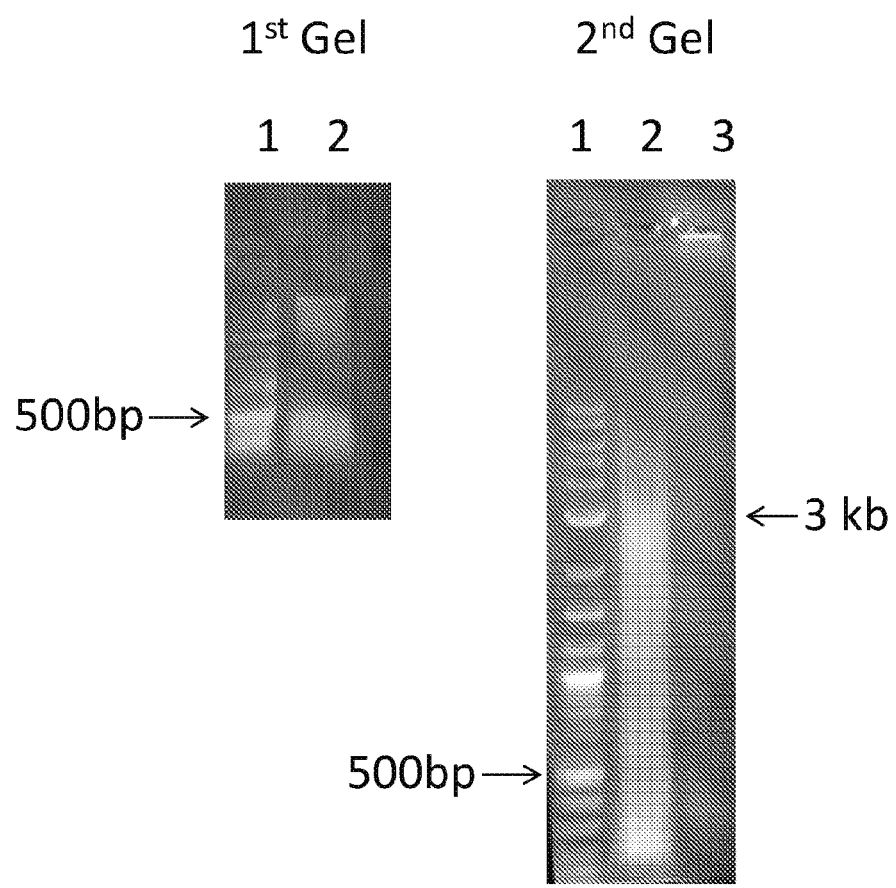
FIG. 14 is an agarose gel electrophoresis visualization of branched and debranched RCA reaction products.

As shown in FIG. 14, debranching with nicking enzymes and polymerase-based extension managed to generate long debranched DNA fragments up to 3 kb, whereas T7 endonuclease I-based debranching produced mostly short fragments (<=500 bp) and some heavy material which is probably remaining undigested branched constructs. Lane 1 in 1$^{st}$ Gel and 2$^{nd}$ Gel of FIG. 14 is the marker (shown in detail in FIG. 16), lane 2 in 1$^{st}$ Gel is the T7 endonuclease I-treated RCA sample; lane 2 in 2$^{nd}$ Gel is the RCA aliquot treated with nicking enzymes and Taq polymerase; and lane 3 in 2$^{nd}$ Gel is the RCA aliquot serving as negative control. The negative control shows a typical heavily branched RCA product that is stuck in the gel's well.

Example 3

Generating dsDNA constructs comprising multiple copies for nanopore sequencing using RCA and nicking endonucleases:

In one example, whole genomic lambda phage DNA material was fragmented using dsDNA fragmentase (New England BioLabs),), producing fragments with an average length of approximately 500 bp. The fragmented material was purified using Magjet magnetic beads (Thermo Fisher) and incubated with T4 DNA polymerase, T4 PNK and Taq polymerase in NEBuffer 2 (New England BioLabs) comprising dNTPs and ATP, first at 25° C. to allow end repair and then at 72° C. to allow dA-tailing. The sample was then incubated with T4 DNA ligase using the Quick ligation kit (New England BioLabs), and hairpin adaptors with dT overhangs and loops comprising the sequence CCTCAGC which is recognized and nicked by Nt.BbvCI when present in dsDNA. A few microliters of the ligation reaction were used for RCA using phi29 DNA polymerase and PrimPol (Sygnis) in CutSmart buffer (New England BioLabs), at 30° C. The polymerase was inactivated with brief incubation at 65° C. Nt.BbvCI was added directly to the RCA sample, and incubated at 37° C. The reaction was added Taq polymerase and (2/3)× ThermoPol buffer II and incubated at 68° C., then at 80° C. to inactivate the nicking enzymes. The sample was directly placed on the filter of an Oligo Clean & Concentrator™ column (Zymo Research) and briefly centrifuged, to get rid of remaining hyperbranch material of large size.

Figure 15:
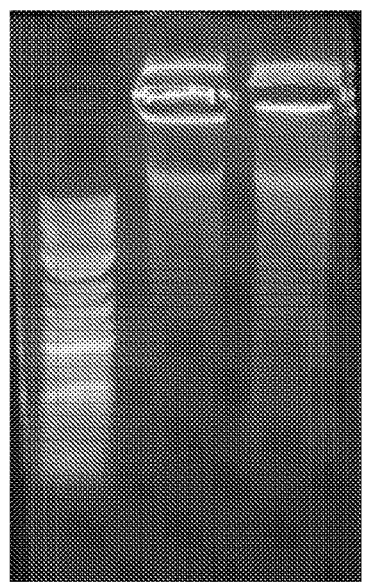
FIG. 15 is an agarose gel electrophoresis visualization of branched and debranched RCA reaction products.

FIG. 15, lane 2, shows untreated RCA, and lane 3 shows RCA treated with Nt.BbvCI and Taq polymerase (not passing through a column) according to protocol. It is evident that the treated sample comprises debranched material migrating faster in the agarose gel.

In other examples, nicking enzyme inactivation can precede Taq extension.

In certain examples, extension with Taq and nicking enzyme inactivation can be followed by addition of Nb.BbvCI to the same buffer, incubation at 37° C., and inactivation at 80° C., then extension with Taq polymerase again, to further debranch any remaining unresolved structures.

In other examples, the starting material is not genomic DNA, but PCR sample.

The sample was then directly used for ligation to adaptors for nanopore sequencing with MinION sequencer (Oxford Nanopore Technologies) Specifically, 30 µl of sample were added to 20 µl AMXID reagent (iD assay kit; Oxford Nanopore Technologies) and 50 µl Blunt/TA mix (New England BioLabs) and incubated at 25° C. for 20 min to allow for adaptor ligation. Then, 40 µl AMPure XP beads (Beckman Coulter) were added, mixed by pipetting, incubated at room temperature with mild rotation for 5 min, then placed on a magnet to separate the beads. After the supernatant was discarded, the beads were resuspended in 140 µl ABB reagent (Oxford Nanopore Technologies), and placed on a magnet, had their supernatant discarded, then added ABB reagent again and placed on a magnet After the supernatant was discarded, 14 µl elution buffer ELB (Oxford Nanopore Technologies) was added to the beads and incubated at room temperature for 10 min. Then the beads were placed on a magnet, and 12 µl of the retrieved supernatant was placed in 37.5 µl RBF buffer and 25.5 µl LLB reagent.

The resulting mix was loaded in a MinION R9.4 flow cell per manufacturer's protocol. The flow cell was placed in a MinION sequencer which was plugged to a USB port of a computer meeting the specifications provided by Oxford Nanopore Technologies. The sequencing run was managed by the MinKNOW software, which produced fast5 files comprising raw readings that were subsequently used by the Metrichor software to carry out basecalling. The basecalling results were stored in fast5 files, from which a FASTA file with the sequence information for each read was generated by using "poretools" software according to authors' instructions (poretools.readthedocs.io/en/latest/) (Loman and Quinlan, 2014).

The sequencing run lasted approximately 9 hours and produced 53,580 reads, whose sequences were stored in the "poretook"-generated FASlA file. Each sequence comprised one or more (whole or partial) copies ofone original DNA fragment or part of one original DNA fragment. In order to identify the copies within each sequence, each sequence was subjected to blastn alignment to the lambda phage genome. Blastn is well known to those skilled in the art Blastn was run for each sequence in theFASTA file, per software instructions (ncbi nlm nih gov/books/NBK279675/) The output of blastn was a text file comprising all alignment results each ofwhich represented a single copy of an original DNA fragment. A single alignment result (orresponding to a single copy of an original DNA fragment) comprised the sequence ofthe copy, its size, its position on the read (ie sequence in the FASTA file) that was subjected to blastn, its position on the lambda phage genome, and the identifier of the read that it belongs to. Using R software functions well known to those skilled in the art (r-project.org/), the number of copies per sequence was determined from the blastn output file, for each sequence that was subjected to blastn-based analysis. Approximately 92% of the reads(sequences in the FASTA file) had 2 or more copies, whereas 53% of the reads had 6 or more copies. 6 copies are usually needed to achieve accuracy more than 99.9%, by generating a consensus sequence from these copies (Travers et al., 2010) Generating consensus by aligning 2 or more similar sequences(in this case, the sequences of 2 or more copies originating from a single original DNA fragment) is well known to those skilled in the art (Yu and Hwa, 2001); (Travers et al., 2010). For example, the sequences of multiple copies can be processed to produced a multiple alignment by using appropriate software and algorithms such as Clustal Omega (clustal org/omega/); (Sievers et al., 2011). Such a multiple alignment can be used to generate a consensus sequence by using software and algorithms well known to those skilled in the art, such as the"cons" function of EMBOSS (emboss sourceforge net/); (ebi.ac.uk/Tools/emboss/); (bioinformatics.nl/cgi-bin/emboss/help/cons), (Rice et al., 2000).

In other examples, at least two different nicking-and-extension reactions are pooled to correct for any bias arising from nicking sites within the template DNA to be sequenced. For example, one reaction comprises Nt.BbvCI and/or Nb.BbvCI, and the other reaction comprises Nt.BsmAI.

One major advantage of this method is that it is a single-tube protocol, not requiring purifications between enzymatic reactions.

Example 4

Generating dsDNA constructs comprising multiple copies for nanopore sequencing using resolvases:

Resolvases can be active in a variety of buffers, so that they can be conveniently used in single-tube reactions [idtdna.com/pages/docs/default-source/catalog-product-documentation/crispr-mutation-detection.pdf?sfvrsn=7]; [nzytech.com/wp-content/uploads/woocommerce_uploads/2015/12/MB212_T7-Endonuclease-I.pdf?187cbf].

In one example, whole genomic DNA is fragmented using dsDNA fragmentase (New England BioLabs). The fragmented material is purified using Magjet magnetic beads (Thermo Fisher) and incubated with T4 DNA polymerase, T4 PNK and Taq polymerase in NEBuffer 2 (New England BioLabs) comprising dNTPs and ATP, first at 25° C. to allow end repair and then at 72° C. to allow dA-tailing. The sample is then incubated with T4 DNA ligase using the Quick ligation kit (New England BioLabs), and hairpin adaptors.

A few microliters of the ligation reaction are used for RCA using phi29 DNA polymerase and PrimPol in CutSmart Buffer, at 30° C. The polymerase is inactivated with brief incubation at 65° C. Optionally, rSAP is added to the solution after RCA and incubated at 37° C. to dephosphorylate dNTPs, thereby preventing any future priming by PrimPol. In other examples, RCA can be conducted by using primers with or without phosphorothioates and optionally degrading primers afterwards by adding exonuclease VII or T respectively to the solution. T7 endonuclease I is added directly to the solution and incubated at 37° C. In the event that 14 endonuclease VII is used, beta-ME may be added [affymetrix.com/catalog/131312/USBiT4+Endonuclease+4VII+T4+gp49-Holiday+Junction+Resolvase #1_1]. In order to preserve the integrity of nicked, gapped or flapped structures or other intermediate products created by endonuclease cleavage and prevent their further degradation to shorter products, the incubation with endonuclease can occur concurrently with extension and/or ligation, by introducing polymerases such as DNA Pol I and/or ligases such as T4 DNA ligase to the reaction. Alternatively, thermostable resolvases can be used, such as *Thermus thermophilus* RuvC, in combination with thermostable polymerases and/or ligases such as Taq polymerase or Bst full length DNA polymerase, and Taq ligase respectively.

Figure 16:
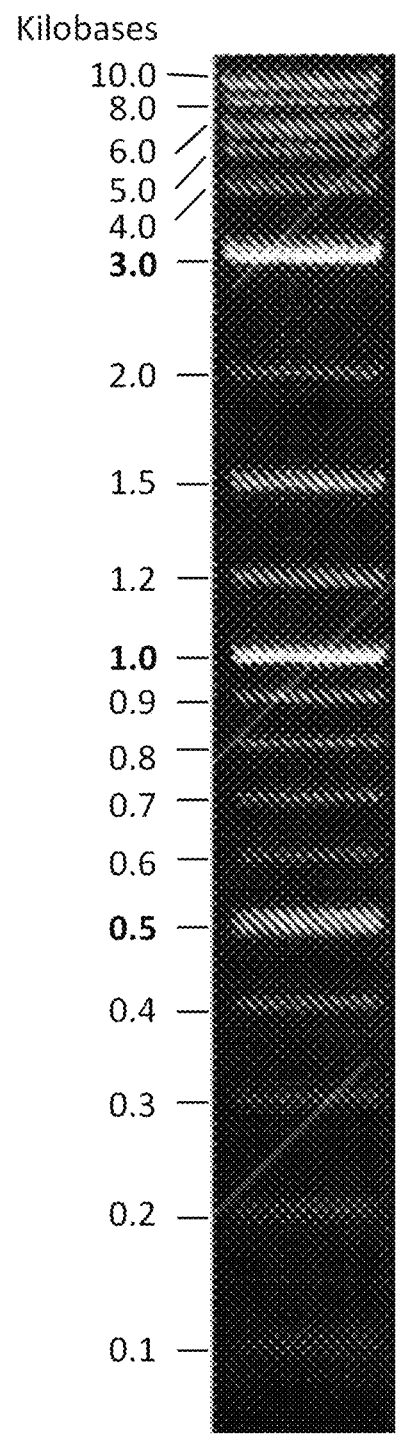
FIG. 16 is an image of the DNA ladder used in the experiments described herein.

FIG. 16 shows the Quick Load 2-log DNA ladder (New England BioLabs) used in all the experiments shown herein.

All the methods disclosed and claimed herein may comprise washing steps, reagent exchange steps and other treatments in between described steps as recognized and known by those skilled in the art.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations can be applied to the compositions and methods and in the steps or in the sequence of steps of the methods described herein without departing from the concept, spirit and scope of the disclosure. More specifically, it will be apparent that certain agents which are both chemically related can be substituted for the agents described herein while the same or similar results would be achieved. All such similar substitutes and modifications apparent to those skilled in the art are deemed to be within the spirit, scope and concept of the disclosure as defined by the appended claims.

REFERENCES

Barnes, C., Earnshaw, D. J., Liu, X., Milton, J., Ost, T. W. B., Rasolonjatovo, I. M. J., Rigatti, R., Romieu, A., Smith, G. P., Turcatti, G., Worsley, G J., Wu, X., 2007. Preparation of templates for nucleic acid sequencing WO2007010251 A3

Beaucage, S. L., Iyer, R. P., 1993. The Functionalization of Oligonucleotides Via Phosphoramidite Derivatives. Tetrahedron 49, 1925-1963. doi 10.1016/S0040-4020(01)86295-5

Benner, S. A., 1993. Oligonucleotide analogs containing sulfur linkages. U.S. Pat. No. 5,216,141 A.

Berg, J. L. T. L. S. J., 2006. Biochemistry 6th Edition (Sixth Ed.) 6e By Jeremy Berg, John Tymoczko & Lubert Stryer 2006. Example Product Manufacturer.

Brill, W. K. D., Tang, J. Y., Ma, Y. X., Caruthers, M. H., 1989. Synthesis of oligodeoxynucleoside phosphorodithioates via thioamidites. J. Am. Chem. Soc. 111, 2321-2322, doi:10.1021/ja00188a066

Carlsson, C, Jonsson, M., Nord6n, B., Dulay, M T, Zare, R. N., Noolandi, J., Nielsen, P. E., Tsui, L.-C., Zielenski, J., 1996. Screening for genetic mutations. Nature 380, 207-207. doi.10.1038/380207a0

Caruccio, N., 2011. Preparation of Next-Generation Sequencing Libraries Using Nextera™ Technology: Simultaneous DNA Fragmentation and Adaptor Tagging by In Vitro Transposition, in: Kwon, Y. M., Ricke, S. C. (Eds.), High-Throughput Next Generation Sequencing, Methods in Molecular Biology. Humana Press, pp. 241-255

Cook, P. D., Acevedo, O., Hebert, N., 1997. Phosphoramidate and phosphorothioamidate oligomeric compounds. U.S. Pat. No. 5,637,684 A.

Cook, P. D., Sanghvi, Y S., 1992. Nuclease resistant, pyrimidine modified oligonucleotides that detect and modulate gene expression WO1992002258 A1.

De Mesmaeker, A., Waldner, A., S. Sanghvi, Y., Lebreton, J., 1994. Comparison of rigid and flexible backbones in antisense oligonucleotides. Bioorg. Med. Chem. Lett. 4, 395-398. doi:10.1016/0960-894X(94)80003-0

Dempcy, R. O., Browne, K. A., Bruice, T. C., 1995. Synthesis of a thymidyl pentamer of deoxyribonucleic guanidine and binding studies with DNA homopolynucleotides. Proc Natl Acad. Sci. 92,6097-6101.

Dieffenbach, C. W., Dveksler, G. S., 2003. PCR Primer: A Laboratory Manual, 2 Lab edition. ed. Cold Spring Harbor Laboratory Press, Cold Spring Harbor, N Y.

Drmanac, R., Callow, M., 2013. Nucleic acid sequencing and process. U.S. Pat. No. 8,518,640 B2.

Eckstein, F. (Ed.), 1992. Oligonucleotides and Analogues: A Practical Approach. Oxford University Press, Oxford; New York.

Egholm, M., Buchardt, O., Christensen, L., Behrens, C., Freier, S. M., Driver, D. A., Berg, R. H., Kim, S. K., Norden, B., Nielsen, P. E., 1993. PNA hybridizes to complementary oligonucleotides obeying the Watson-Crick hydrogen-bonding rules. Nature 365, 566-568. doi: 10.1038/365566a0

Egholm, M., Buchardt, O., Nielsen, P. E., Berg, R. H., 1992. Peptide nucleic acids (PNA). Oligonucleotide analogs with an achiral peptide backbone. J. Am. Chem. Soc. 114, 1895-1897. doi:10.1021/ja00031a062

Gait, M. J. (Ed), 1984. Oligonucleotide Synthesis: A Practical Approach Oxford University Press, Oxford Oxfordshire; Washington, DC.

Gao, X., Jeffs, P. W., 1994. Unusual conformation of a 3'-thioformacetal linkage in a DNA duplex. J. Biomol. NMR 4, 17-34. doi:10.1007/BF00178333

Goodwin, S., Gurtowski, J., Ethe-Sayers, S., Deshpande, P., Schatz, M., McCombie, W. R., 2015. Oxford Nanopore Sequencing and de novo Assembly of a Eukaryotic Genome. bioRxiv 013490. doi:10.1101/013490

Green, E. D., 1997. Genome Analysis: A Laboratory Manual. Cold Spring Harbor Laboratory Press.

Green, M. R., Sambrook, J., 2012 Molecular Cloning: A Laboratory Manual (Fourth Edition): Three-volume set, 4th edition. ed. Cold Spring Harbor Laboratory Press, Avon, Mass.

Harris, T. D., 2010. Enhancing resolution of sequence analysis of short DNA stretches via difined length spacers; genetic mapping and genomics. U.S. Pat. No. 7,767,400 B2.

Higgins, L. S., Besnier, C., Kong, H., 2001. The nicking endonucleaseN.BstNBI is closely related to Type Its restriction endonucleases MlyI and PleI. Nucleic Acids Res. 29, 2492-2501.

Horn, T., Chaturvedi, S., Balasubramaniam, T. N., Letsinger, R L, 1996. Oligonucleotides with alternating anionic and cationic phosphoramidate linkages: Synthesis and hybridization of stereo-uniform isomers. Tetrahedron Lett. 37,743-746. doi:10.1016/0040-4039(95)02309-7

Jenkins, G. N., Turner, N.J., 1995. The biosynthesis of carbocyclic nucleosides. Chem Soc. Rev. 24, 169-176. doi:10.1039/CS9952400169

Jung, P. M., Histand, G., Letsinger, R. L., 1994. Hybridization of Alternating Cationic/Anionic Oligonucleotides to RNA Segments. Nucleosides Nucleotides 13, 1597-1605. doi:10.1080/15257779408012174

Kornberg, A., Baker, T. A., 2005. DNA Replication. University Science Books.

Koshkin, A. A., Nielsen, P., Meldgaard, M., Rajwanshi, V. K., Singh, S. K., Wengel, J., 1998. LNA (Locked Nucleic Acid): An RNA Mimic Forming Exceedingly Stable LNA:LNA Duplexes. J. Am. Chem. Soc. 120, 13252-13253. doi:10.1021/ja9822862

Letsinger, R. L., Bach, S. A., Eadie, J. S., 1986. Effects of pendant groups at phosphorus on binding properties of d-ApA analogues. Nucleic Acids Res. 14, 3487-3499 doi:10.1093/nar/14.8.3487

Letsinger, R. L., Mungall, W. S., 1970. Nucleotide chemistry. XVI. Phosporamidate analogs of oligonucleotides. J. Org. Chem. 35, 3800-3803. doi:10.1021/jo00836a048

Letsinger, R. L., Singman, C. N., Histand, G., Salunkhe, M., 1988. Cationic oligonucleotides. J. Am. Chem. Soc. 110, 4470-4471. doi:10.1021/ja00221a089

Li, C., Chng, K. R., Boey, E. J. H., Ng, A. H. Q., Wilm, A., Nagarajan, N., 2016a. INC-Seq: accurate single molecule reads using nanopore sequencing. GigaScience 5, 34. doi:10.1186/s13742-016-0140-7

Li, C., Chng, K. R., Boey, J. H. E., Ng, H. Q. A., Wilm, A., Nagarajan, N., 2016b. INC-Seq: Accurate single molecule reads using nanopore sequencing. bioRxiv. doi:10.1101/038042

Loeb, L. A., Hood, L., Suzuki, M., 2002 Thermostable polymerases having altered fidelity and method of identifying and using same. U.S. Pat. No. 6,395,524 B2.

Mag, M, Silke, L, Engels, J. W., 1991. Synthesis and selective cleavage of an oligodeoxynucleotide containing a bridged internucleotide 5'-phosphorothioate linkage. Nucleic Acids Res. 19, 1437-1441. doi:10.1093/nar/19.7.1437

Ma, P. N.-T., 2013. Methods, compositions, and kits for amplifying and sequencing polynucleotides. U.S. Pat. No. 8,486,627 B2

Meier, C., Engels, J. W., 1992. Peptide Nucleic Acids (PNAs)-Unusual Properties of Nonionic Oligonucleotide Analogues. Angew. Chem. Int. Ed. Engl. 31, 1008-1010. doi:10.1002/anie.199210081

Mesmaeker, A. D., Lebreton, J., Waldner, A., Cook, P. D., 1997. Backbone modified oligonucleotide analogs. U.S. Pat. No. 5,602,240 A.

Nelson, D. L., Cox, M. M., 2012. Lehninger Principles of Biochemistry, Sixth Edition edition. ed. W.H. Freeman, New York.

Patel, P. H., Loeb, L. A., 2003. Mutant enzymatic protein for use as tool in human therapeutics and diagnostics. U.S. Pat. No. 6,602,695 B2.

Patel, P. H., Loeb, L. A., 2001. A mutant polymerase having asptyrserglnilegluleuarg amino acid sequence in the active site and possesses altered fidelity or altered catalytic activity. U.S. Pat. No. 6,329,178 B1.

Peters, B A., Kermani, B. G, Sparks, A. B, Alferov, O., Hong, P., Alexeev, A, Jiang, Y, Dahl, F., Tang, Y. T., Haas, J., Robasky, K., Zaranek, A. W., Lee, J.-H., Ball, M. P., Peterson, J E., Perazich, H., Yeung, G., Liu, J., Chen, L., Kennemer, M. I., Pothuraju, K., Konvicka, K., Tsoupko-Sitnikov, M., Pant, K. P., Ebert, J. C, Nilsen, G B., Baccash, J., Halpern, A. L., Church, G. M., Drmanac, R., 2012. Accurate whole-genome sequencing and haplotyping from 10 to 20 human cells. Nature 487, 190-195. doi:10.1038/naturel1236

PICHER, A. J., Blanco, L., 2014. Methods for amplification and sequencing using thermostable tthprimpol. WO2014140309 A1

Quake, S., 2011. Methods and kits for analyzing polynucleotide sequences. U.S. Pat. No. 7,981,604 B2.

RAWLS, R. L., 1997. OPTIMISTIC ABOUT ANTISENSE. Chem. Eng. News Arch. 75, 35-39. doi:10.1021/cen-v075n022.p035

Rice, P. A., Correll, C. C., 2008. Protein-Nucleic Acid Interactions: Structural Biology. Royal Society of Chemistry.

Schmidt, V. K., Sørensen, B. S., Sorensen, H. V., Alsner, J., Westergaard, O., 1994. Intramolecular and intermolecular DNA ligation mediated by topoisomerase II. J. Mol. Biol. 241, 18-25 doi:10.1006/jmbi.1994.1469

Sprinzl, M., Stembach, H., Von Der Haar, F., Cramer, F., 1977. Enzymatic Incorporation of ATP and CTP Analogues into the 3' End of tRNA. Eur J. Biochem. 81, 579-589. doi:10.1111/j.1432-1033.1977.tb11985.x Summerton, J. E., Weller, D. D., 1991. Uncharged morpholino-based polymers having achiral intersubunit linkages. U.S. Pat. No. 5,034,506 A.

Summerton, J. E., Weller, D. D., Stirchak, E P., 1993 Alpha-morpholino ribonucleoside derivatives and polymers thereof. U.S. Pat. No. 5,235,033 A.

Ts'o, P O. P., Miller, P. S., 1984. Nonionic nucleic acid alkyl and aryl phosphonates and processes for manufacture and use thereof. UJS4469863 A.

von Kiedrowski, G, Wlotzka, B, Helbing, J., Matzen, M., Jordan, S., 1991. Parabolic Growth of a Self-Replicating Hexadeoxynucleotide Bearing a 3'-5'-Phosphoamidate Linkage. Angew. Chem. Int. Ed. Engl. 30, 423-426. doi:10.1002/anie.199104231

Williams, J., Anderson, J., Urlacher, T., Steffens, D., 2007. Mutant polymerases for sequencing and genotyping. US20070048748 A1.

Williams, P., Hayes, M. A., Rose, S. D., Bloom, L. B., Reha-Krantz, L. J., Pizziconi, V. B., 2006. Sequencing DNA using polymerase, fluorescence, chemiluminescence, thermopile, thermistor and refractive index measurements; microcalorimetric detection. U.S. Pat. No. 7,037,687 B2

Wyatt, H. D M., West, S. C., 2014. Holliday Junction Resolvases. Cold Spring Harb Perspect Biol. 6. doi: 10.1101/cshperspect.a023192

Yau, E. K., 1997. Process for preparing phosphorothioate oligonucleotides. U.S. Pat. No. 5,644,048 A.

Zhang, K., Martiny, A. C., Reppas, N. B., Barry, K. W., Malek, J., Chisholm, S. W., Church, G. M., 2006. Sequencing genomes from single cells by polymerase cloning Nat. Biotechnol. 24, 680-686. doi:10.1038/nbt1214

SEQUENCE LISTING

<160> NUMBER OF SEQ ID NOS: 1

<210> SEQ ID NO 1
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 1
ctcacacact ttttttgaga gagagagaga gagagatttc ctcagctttt gtgtgtgag     59

Rigatti, R., Ost, T. W. B., 2010. Method for pair-wise sequencing a plurality of target polynucleotides. U.S. Pat. No. 7,754,429 B2

Sanghvi, Y. S., Cook, P. D. (Eds.), 1994. Carbohydrate Modifications in Antisense Research. American Chemical Society, Washington, DC.

Sawai, H., 1984. SYNTHESIS AND PROPERTIES OF OLIGOADENYLIC ACIDS CONTAINING 2′-5′ PHOSPHORAMIDE LINKAGE Chem Lett. 13, 805-808. doi:10.1246/cl.1984.805

What is claimed is:

1. A method comprising steps of:

(i) producing a circularized nucleic acid molecule by attaching a nucleic acid molecule to at least one adaptor comprising at least one nicking endonuclease recognition site and circularizing the nucleic acid molecule;

(ii) performing a rolling-circle amplification by exposing the circularized nucleic acid molecule to nucleotides, strand-displacing polymerases, and at least one primer, thereby producing one or more double-stranded nucleic acid constructs;

(iii) exposing the one or more double-stranded nucleic acid constructs produced in step (ii) to nicking endonucleases that recognize the at least one nicking endonuclease recognition site present in the one or more double-stranded nucleic acid constructs produced in step (ii) such that at least one nick is produced on only one strand of double-stranded regions of the one or more double-stranded nucleic acid constructs produced in step (ii), thereby producing one or more nicked nucleic acid constructs; and (iv) exposing the one or more nicked nucleic acid constructs of step (iii) to polymerases comprising 5'-3' exonuclease and/or flap endonuclease activity.

2. The method according to claim 1, further comprising directly performing ligation of the one or more nucleic acid constructs produced in step (iv) to adaptors.

3. The method according to claim 1, wherein steps (i)-(ii), (ii)-(iii), or (i)-(iii) are conducted in a single-tube reaction.

4. The method according to claim 1, wherein steps (i) to (iv) are conducted in a single-tube reaction, and wherein the method does not comprise a purification process to remove the strand-displacing polymerases between steps (ii) and (iii) and/or does not comprise a purification process to remove the nicking endonucleases between steps (iii) and (iv).

* * * * *